(12) United States Patent
Kiefer et al.

(10) Patent No.: US 8,329,398 B2
(45) Date of Patent: Dec. 11, 2012

(54) UNIVERSAL AMPLIFICATION OF FRAGMENTED RNA

(75) Inventors: Michael C. Kiefer, Clayton, CA (US); Kenneth W. Hoyt, Burlingame, CA (US)

(73) Assignee: Genomic Health, Inc., Redwood City, CA (US)

( * ) Notice: Subject to any disclaimer, the term of this patent is extended or adjusted under 35 U.S.C. 154(b) by 559 days.

(21) Appl. No.: 11/959,251

(22) Filed: Dec. 18, 2007

(65) Prior Publication Data
US 2009/0042192 A1   Feb. 12, 2009

Related U.S. Application Data

(63) Continuation of application No. 11/020,946, filed on Dec. 21, 2004, now abandoned.

(60) Provisional application No. 60/532,684, filed on Dec. 23, 2003.

(51) Int. Cl.
C12Q 1/68   (2006.01)
C07H 21/02  (2006.01)

(52) U.S. Cl. .................. 435/6.1; 435/91.1

(58) Field of Classification Search .......... None
See application file for complete search history.

(56) References Cited

U.S. PATENT DOCUMENTS

| | | | |
|---|---|---|---|
| 4,699,877 A | 10/1987 | Cline et al. | 435/6 |
| 5,015,568 A | 5/1991 | Tsujimoto et al. | 435/5 |
| 5,200,313 A * | 4/1993 | Carrico | 435/6 |
| 5,459,251 A | 10/1995 | Tsujimoto et al. | 536/23.5 |
| RE35,491 E | 4/1997 | Cline et al. | 435/6 |
| 5,858,678 A | 1/1999 | Chinnadurai | 435/7.1 |
| 5,952,179 A | 9/1999 | Chinnadurai | 435/6 |
| 5,985,553 A | 11/1999 | King et al. | 435/6 |
| 6,114,149 A * | 9/2000 | Fry et al. | 435/91.2 |
| 6,207,452 B1 | 3/2001 | Govindaswamy | 435/330 |
| 6,271,002 B1 | 8/2001 | Linsley et al. | 435/91.1 |
| 6,322,986 B1 | 11/2001 | Ross | 435/6 |
| 6,351,712 B1 * | 2/2002 | Stoughton et al. | 702/19 |
| 6,414,134 B1 | 7/2002 | Reed | 536/24.5 |
| 6,582,919 B2 | 6/2003 | Danenberg | 435/6 |
| 6,602,670 B2 | 8/2003 | Danenberg | 435/6 |
| 6,618,679 B2 | 9/2003 | Loehrlein et al. | 702/20 |
| 2002/0009736 A1 | 1/2002 | Wang | 435/6 |
| 2003/0022318 A1* | 1/2003 | Lin et al. | 435/91.2 |
| 2003/0073112 A1 | 4/2003 | Zhang et al. | 435/6 |
| 2003/0104499 A1 | 6/2003 | Pressman et al. | 435/7.23 |

(Continued)

FOREIGN PATENT DOCUMENTS

EP   0 108 564 B1   5/1988

(Continued)

OTHER PUBLICATIONS

Lee et al. (Journal of Biological Chemistry, 1998, vol. 273, No. 39, p. 25261-25271).*

(Continued)

*Primary Examiner* — Stephanie K Mummert
(74) *Attorney, Agent, or Firm* — James S. Keddie; Carol L. Francis; Bozicevic, Field & Francis, LLP

(57) ABSTRACT

The invention relates to methods of using fragmented RNA, such as RNA obtained from archived fixed paraffin-embedded tissue material (FPET RNA) or other clinically biopsied tissue specimens for universal gene expression profiling.

10 Claims, 24 Drawing Sheets

U.S. PATENT DOCUMENTS

| | | | | |
|---|---|---|---|---|
| 2003/0162214 | A1* | 8/2003 | Heller et al. | 435/6 |
| 2003/0165952 | A1 | 9/2003 | Linnarsson et al. | 435/6 |
| 2003/0180791 | A1 | 9/2003 | Chinnadurai | 435/6 |
| 2003/0198970 | A1 | 10/2003 | Roberts | 435/6 |
| 2004/0009489 | A1 | 1/2004 | Golub et al. | 435/6 |
| 2004/0133352 | A1 | 7/2004 | Bevilacqua et al. | 702/19 |

FOREIGN PATENT DOCUMENTS

| | | |
|---|---|---|
| EP | 1 365 034 | 11/2003 |
| WO | WO 99/02714 | 1/1999 |
| WO | WO 00/50595 | 8/2000 |
| WO | WO 00/55173 | 9/2000 |
| WO | WO 01/25250 | 4/2001 |
| WO | WO 01/40466 | 6/2001 |
| WO | WO 01/55320 | 8/2001 |
| WO | WO 01/70979 | 9/2001 |
| WO | WO 02/00677 | 1/2002 |
| WO | WO 02/06526 | 1/2002 |
| WO | WO 02/08260 | 1/2002 |
| WO | WO 02/08261 | 1/2002 |
| WO | WO 02/08282 | 1/2002 |
| WO | WO 02/08765 | 1/2002 |
| WO | WO 02/46467 | 6/2002 |
| WO | WO 02/017852 | 7/2002 |
| WO | WO 02/055988 | 7/2002 |
| WO | WO 02/059377 | 8/2002 |
| WO | WO 02/068579 | 9/2002 |
| WO | WO 02/103320 | 12/2002 |
| WO | WO 03/011897 | 2/2003 |
| WO | WO 03/083096 | 10/2003 |
| WO | WO2004/085681 | * 10/2004 |

OTHER PUBLICATIONS

Scorilas (Critical Reviews in Clinical Laboratory Research, 2002, vol. 39, No. 3, p. 193-224).*

Zaug et al. (Nucleic Acids Research, 1996, vol. 24, No. 3, p. 532-533).*

Woods et al. (Nucleic Acids Research, 1977, vol. 4, No. 9, p. 3187-3198).*

Specht et al. (American Journal of Pathology, 2001, vol. 158, No. 2).*

Dietrich et al. (Biotechnology Techniques, 1998, vol. 12, No. 1, p. 49-54).*

Eberwine et al. (PNAS, 1992, vol. 89, p. 3010-3014).*

Rychlik et al. (Nucleic Acids Research, 1990, vol. 18, No. 21, p. 6409-6412).*

Specht et al. (Am. J of Path, 2001, 158(2):419-429).*

Ohara et al. (Ohara, PNAS et al. 1989, 86, p. 5673-5676).*

Beer et al.,"Gene Expression Profiles Predict Survival of Patients with Lung Adenocarcinoma", Nature Medicine, vol. 8, pp. 816-824, Aug. 2002.

Bhattacharjee et al., "Classification of human lung carcinomas by mRNA expression profiling reveals distinct adenocarcinoma subclasses", Proceedings of the National Academy of Sciences of USA, vol. 98, No. 24, pp. 13790-13795, Nov. 20, 2001.

Golub et al., "Molecular Classification of Cancer: Class Discovery and Class Prediction by Gene Expression Monitoring", Science, vol. 286, pp. 531-537, Oct. 15, 1999.

Hod, A., "Simplified Ribonuclease Protection Assay", Biotechniques, vol. 13, pp. 852-854, 1992.

Lewis et al.,"Unlocking the archive—gene expression in paraffin-embedded tissue", Journal of Pathology, vol. 195, pp. 66-71, 2001.

Martin et al., "Linking Gene Expression Patterns to Therapeutic Groups in Breast Cancer", Cancer Research, vol. 60, pp. 2232-2238, Apr. 15, 2000.

Parker & Barnes, "mRNA: Detection by In Situ and Northern Hybridization", Methods in Molecular Biology, vol. 106, pp. 247-283, 1999.

Ramaswamy et al., "Multiclass cancer diagnosis using tumor gene expression signatures", Proceedings of the National Academy of Sciences of USA, vol. 98, No. 26, pp. 15149-15154, Dec. 18, 2001.

Schena et al., "Parallel human genome analysis: Microarray-based expression monitoring of 1000 genes", Proc. Natl. Acad. Sci. USA, vol. 93, pp. 10614-10619, Oct. 1996.

Sorlie et al., "Gene Expression patterns of breast carcinomas distinguish tumor subclass with clinical implications", Proceedings of the National Academy of Sciences of USA, vol. 98, No. 19, pp. 10869-10874, Sep. 11, 2001.

van't Veer et al., "Gene Expression Profiling Predicts Clinical Outcome of Breast Cancer", Nature, vol. 415, pp. 530-536, Jan. 31, 2002.

Weis et al.,"Detection of rare mRNAs via quantitative RT-PCR", Trends in Genetics, vol. 8, pp. 263-264, Aug. 1992.

West et al., "Predicting the clinical status of human breast cancer by using gene expression profiles", Proceedings of the National Academy of Sciences of USA, vol. 98, No. 20, pp. 11462-11467, Sep. 25, 2001.

Yan et al., "Dissecting Complex Epigenetic Alterations in Breast Cancer Using CpG Island Microarrays", Cancer Research, vol. 61, pp. 8375-8380, Dec. 1, 2001.

Yeang et al., "Molecular Classification of Multiple Tumor Types", Bioinformatics, vol. 17, Suppl. 1, pp. S316-S322, 2001.

Brabender, Jan, et al.; *Epidermal Growth Factor Receptor and HER2-neu mRNA Expression in Non-Small Cell Lung Cancer is Correlated with Survival*, Clinical Cancer Research; vol. 7, Jul. 2001; pp. 1850-1855.

Ding, Chunming, et al.; *A high-throughput gene expression analysis technique using competitive PCR and matrix-assisted laser desorption ionization time-of-flight MS*, PNAS, vol. 100:6; Mar. 18, 2003; pp. 3059-3064.

Cambridge Healthtech Institute Conference Agenda; "Enabling Molecular Profiling With Cellular Resolution: Microgenomics Using Homogeneous Cell Samples"; Dec. 2002; 5 pgs.

Yang, Li, et al.; *BADGE, BeadsArray for the Detection of Gene Expression, a High-Throughput Diagnostic Bioassay*; Genome Research; vol. 11; 2001; pp. 1888-1898.

Japanese Office Action, Nov. 2, 2010, JP App. No. 2006-547324, 7pgs (including English translation).

* cited by examiner

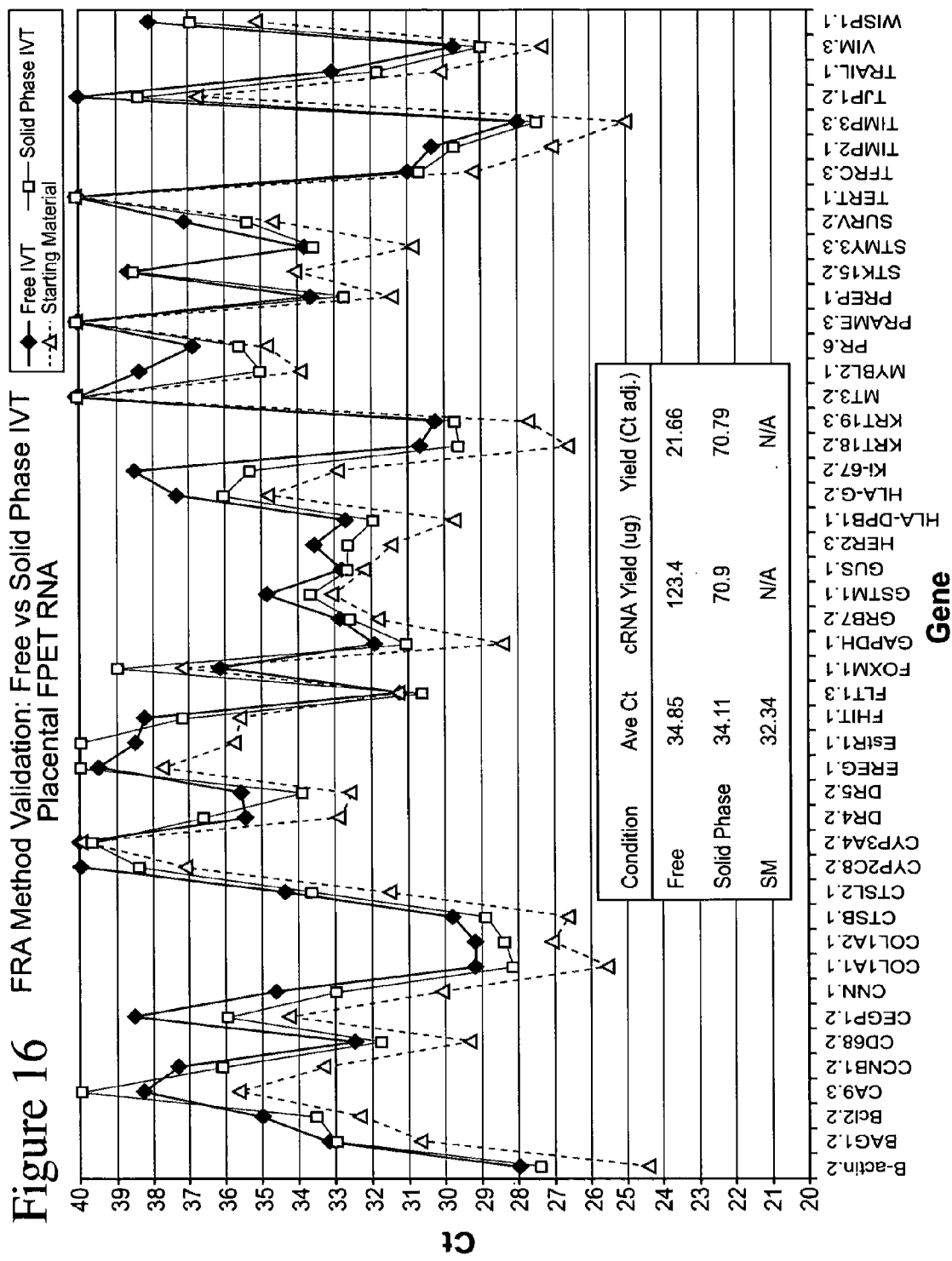
Figure 16 FRA Method Validation: Free vs Solid Phase IVT Placental FPET RNA

UNIVERSAL AMPLIFICATION OF FRAGMENTED RNA

This application is a continuation application of application Ser. No. 11/020,946, filed Dec. 21, 2004, now abandoned which claims priority under 35 U.S.C. §119(e) to provisional application Ser. No. 60/532,684 filed on Dec. 23, 2003, the entire disclosure of which is hereby expressly incorporated by reference.

FIELD OF THE INVENTION

The present invention relates to methods of preparing RNA for gene expression profiling by a variety of methods. The methods of the invention are particularly useful for universal amplification of RNA, including RNA in which one or more RNA species is fragmented and/or blocked at it 3' terminus, such as is obtained from fixed paraffin-embedded tissue (FPET). The methods are also useful for detecting RNA species which lack polyadenylation. In addition, methods of enhanced RT-PCR for useful in gene expression profiling are provided.

DESCRIPTION OF THE RELATED ART

Gene expression profiling is increasingly important both in biological research and in clinical practice. Gene expression profiling has been used to classify various cancer types (see, e.g. Golub et al., *Science* 286:531-537 (1999); Bhattacharjae et al., *Proc. Natl. Acad. Sci. USA* 98:13790-13795 (2001); Chen-Hsiang et al., *Bioinformatics* 17 (Suppl. 1):S316-S322 (2001); Ramaswamy et al., *Proc. Natl. Acad. Sci. USA* 98:15149-15154 (2001); Martin et al., *Cancer Res.* 60:2232-2238 (2000); West et al., *Proc. Natl. Acad. Sci. USA* 98:11462-11467 (2001); Sorlie et al., *Proc. Natl. Acad. Sci. USA* 98:10869-10874 (2001); Yan et al., *Cancer Res.* 61:8375-8380 (2001)), and to predict clinical outcome of cancer, such as breast cancer (Van't Veer et al., Nature 415: 530-536 (2002) and lung cancer (Beer et al., Nat. Med. 8:816-24 (2002)).

The most commonly used methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); microarrays (Schena et al., *Proc. Natl. Acad. Sci. USA* 93(2): 106-149 (1996)), and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Of these, due to its sensitivity, reproducibility, and large dynamic range, real-time RT-PCR is becoming the method of choice for high-throughput, accurate expression profiling.

In many situations where gene expression profiling is potentially useful, there is insufficient material for analysis without prior amplification of RNA. As RNA cannot serve as a template for PCR, the first step in gene expression profiling by RT-PCR is the reverse transcription of the RNA template into cDNA, followed by its exponential amplification in a PCR reaction. The conversion of mRNA to cDNA is typically performed by oligo dT priming of the mRNA in the presence of the reverse transcriptase (RT) enzyme. This step, however, is not effective if the source of mRNA is a fixed, paraffin-embedded tissue sample, which may have been archived as long as 10-20 years, and in which the RNA is badly degraded (Lewis et al., *J. Pathol.* 195:66-71 (2001)).

Because FPET samples are the most widely available source of RNA for gene expression profiling in clinical oncology and because archived FPET samples are an important source of RNA for gene expression profiling in research oncology, there is a critical need for methods that enable and improve the efficacy of gene expression profiling using such tissue samples.

SUMMARY OF THE INVENTION

The present invention provides a sample preparation method that enables global amplification of even very small or very fragmented RNA samples. The method of the invention improve the sensitivity of RNA analysis methods, including RT-PCR and hybridization arrays. Furthermore, the methods of the invention permit the measurement of mRNA levels of all expressed genes including fragmented and/or blocked mRNA species in archived paraffin-embedded tissue samples. This method also permits the measurement of non-polyadenylated mRNA such as histones and non-coding RNAs, such as microRNAs (miRNAs). The invention may additionally include an enhanced reverse transcription step and a modified PCR step that increases the sensitivity of RT-PCR used for gene expression profiling of fragmented RNA samples.

In one aspect, the invention concerns a method for preparing a multiplicity of RNA species, which may include fragmented and/or blocked RNA species, for gene expression analysis comprising the steps of:

(a) polyadenylating the fragmented RNA, and
(b) converting the polyadenylated fragmented RNA obtained in step (a) to cDNA.

Typically, the size of the RNA species within the fragmented RNA is between about 20 bases and about 2000 bases, more frequently between about 50 and about 300 bases.

Polyadenylation can, for example, be performed with *E. coli* polyA polymerase.

Since at least some RNA species within the fragmented RNA may be blocked at their 3' termini, the method of the invention may additionally include a step of deblocking. Deblocking can be performed by using conventional reagents, such as, for example, with a phosphatase enzyme, e.g. calf alkaline phosphatase (CIP), bacterial alkaline phosphatase, shrimp alkaline phosphatase, or variants thereof, or with a polynucleotide kinase (PNK), e.g. T4 polynucleotide kinase (T4 PNK), or variants thereof.

In one embodiment, the polyadenylated fragmented RNA obtained in step (a) above is converted to cDNA by treatment with a reverse transcriptase and oligo-dT primers, where the oligo-dT primers may optionally contain an RNA polymerase promoter (e.g. T7 RNA polymerase promoter) sequence.

In another embodiment, before converting the polyadenylated fragmented RNA obtained in step (a) above to cDNA, the polyadenylating agent, such as CIP, or PNK, is removed.

In a further embodiment, the polyadenylated fragmented RNA is converted to cDNA without prior removal of the polyadenylating agent, such as CIP, or PNK.

In a still further embodiment, the polyadenylated fragmented RNA is enriched, e.g. by removal of rRNA sequences, prior to conversion to cDNA and subsequently to double-stranded cDNA.

In yet another embodiment, the polyadenylated fragmented RNA is immobilized before conversion to a cDNA.

In a particular embodiment, the polyadenylated fragmented RNA is hybridized to a solid phase bead format. If desired, the immobilized polyadenylated fragmented RNA is enriched prior to conversion to cDNA. The enrichment may comprise removal of rRNA sequences by hybridization to bead immobilized complementary rRNA oligonucleotides.

In yet another embodiment, the RNA is mRNA obtained from a fixed, paraffin-embedded tissue sample, such as a tumor sample, where the tumor may be cancer, such as, for example, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, or brain cancer.

The method of the invention may additional comprise the step of (c) PCR amplification using one or more cDNA species present in the cDNA obtained in step (b) above as a template.

In a particular embodiment, PCR amplification comprises about 40 cycles, of which the first five cycles, or the first two to five cycles, or the first two cycles are performed at a lower annealing/extension temperature, such as, at a temperature of about 40° C. to 58° C., e.g. about 50° C.

In another embodiment, the method of the invention further comprises the steps of:

(d) converting the cDNA obtained in step (b) to double-stranded DNA; and (e) amplifying the RNA by subjecting the double-stranded DNA obtained in step (d) to in vitro transcription with an RNA polymerase to obtain amplified complementary RNA (cRNA).

In another embodiment of the method of the invention, the polyadenylated fragmented RNA obtained in step (a) is converted to cDNA by treatment with a reverse transcriptase and extended reverse primers, and the cDNA obtained is amplified by PCR using a forward and a reverse PCR primer and a probe, designed based on a target amplicon.

In another aspect, the invention concerns a method for enhanced cDNA synthesis, comprising converting RNA to cDNA by treatment with a reverse transcriptase and extended primers, and amplifying the cDNA obtained by PCR using a forward and a reverse PCR primer and a probe, designed based on a target amplicon. The RNA may be fragmented, at least part of which may be non-polyadenylated.

In yet another aspect, the invention concerns a method for preparing RNA comprising a multiplicity of RNA species for gene expression analysis comprising the steps of:

(a) polyadenylating said RNA; and (b) converting the polyadenylated RNA to cDNA by reverse transcriptase and oligo dT or oligo dT-T7 primers.

In a still further aspect, the invention concerns a method for preparing RNA comprising a multiplicity of RNA species for gene expression analysis comprising the steps of:

(a) polyadenylating said RNA; and (b) converting the polyadenylated RNA to cDNA by reverse transcriptase and oligo dT-T7 primers containing a T7 RNA polymerase promoter, and (c) subjecting the double-stranded DNA obtained in step (b) to in vitro transcription with a T7 RNA polymerase to obtain amplified complementary RNA (cRNA).

BRIEF DESCRIPTION OF THE DRAWINGS

In FIG. 1, there are three representative protocols (A, B and C) of the invention. Processes A and B start with FPET RNA and involve 1) direct or indirect unblocking of the 3'OH on the terminal nucleotide, 2) poly A tailing of the 3' end, 3) oligo dT-primed double-strand cDNA synthesis with the incorporation of a T7 RNA polymerase promoter, and 4) RNA amplification by in vitro transcription. Process C (middle of diagram) starts with FPET RNA and involves 1) directly synthesizing double-stranded cDNA using T7-(N)15 primers with a T7 RNA polymerase promoter, and 2) RNA amplification by in vitro transcription.

Prior to gene expression analysis, the RNA was treated with PNK (+PNK) or buffer control (−PNK), followed by polyadenylation by EPAP. The RNA was then converted into cDNA with reverse transcriptase and oligo dT primers (+PNK/Oligo dT and −PNK/Oligo dT) or gene specific primers (+PNK/GSP and −PNK/GSP). Relative yields are measured by the threshold cycle (Ct). Inset: Agilent 2100 gel image of FPET RNA treated with PNK or buffer control followed by EPAP. Lane M shows RNA markers with the size of each band denoted in bases.

Figure 8:
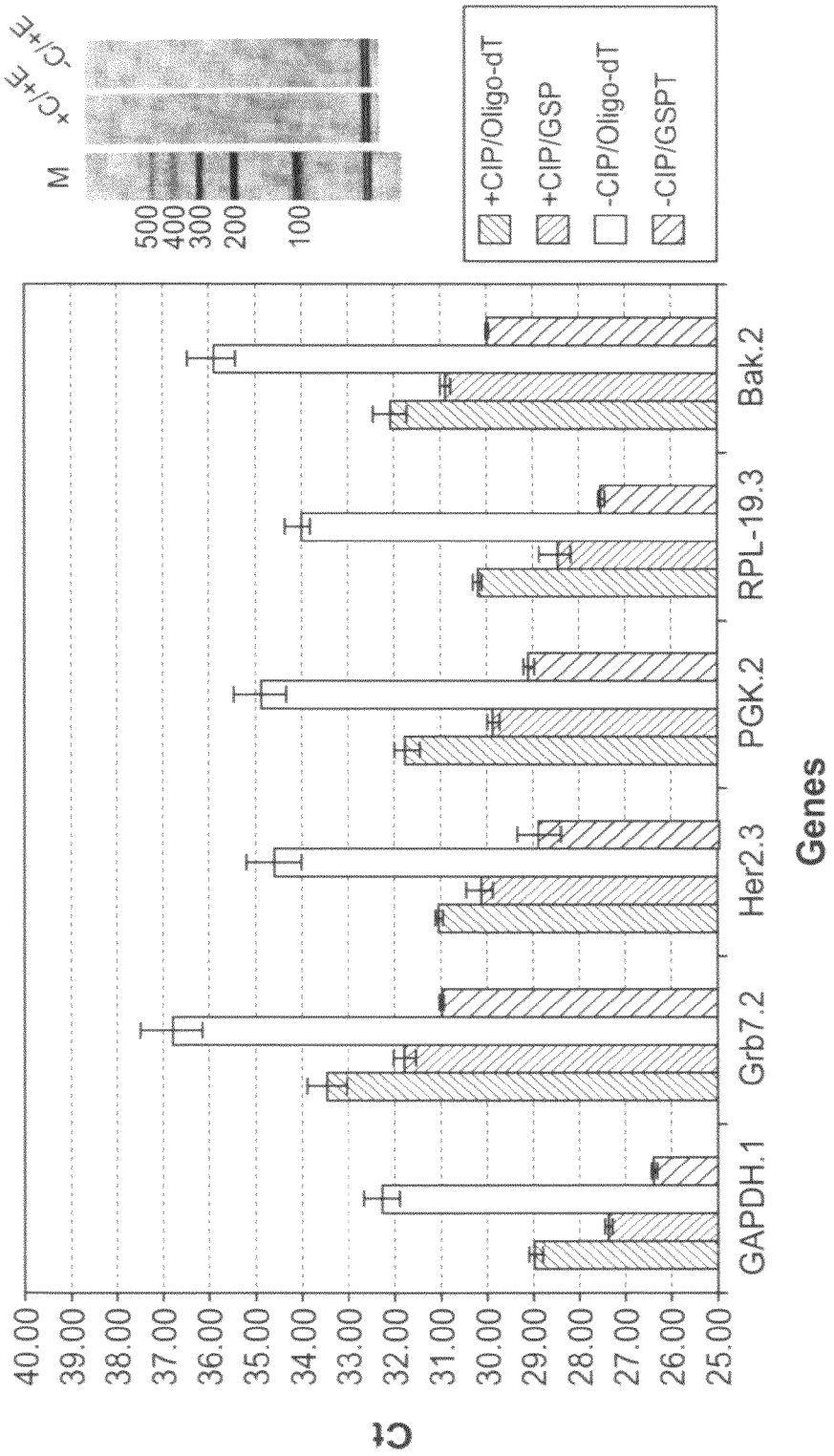
Figure 9A:
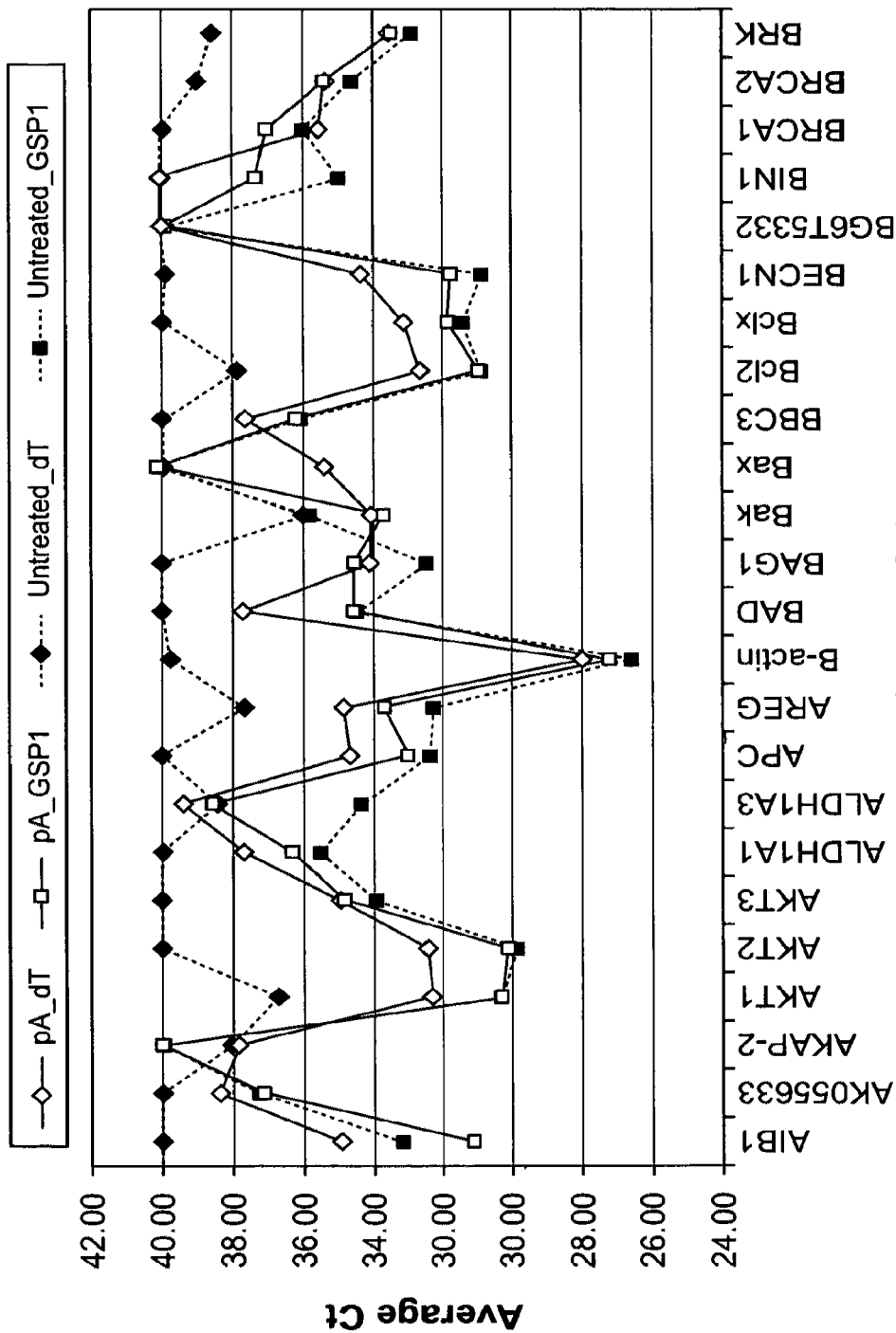
Figure 9B:
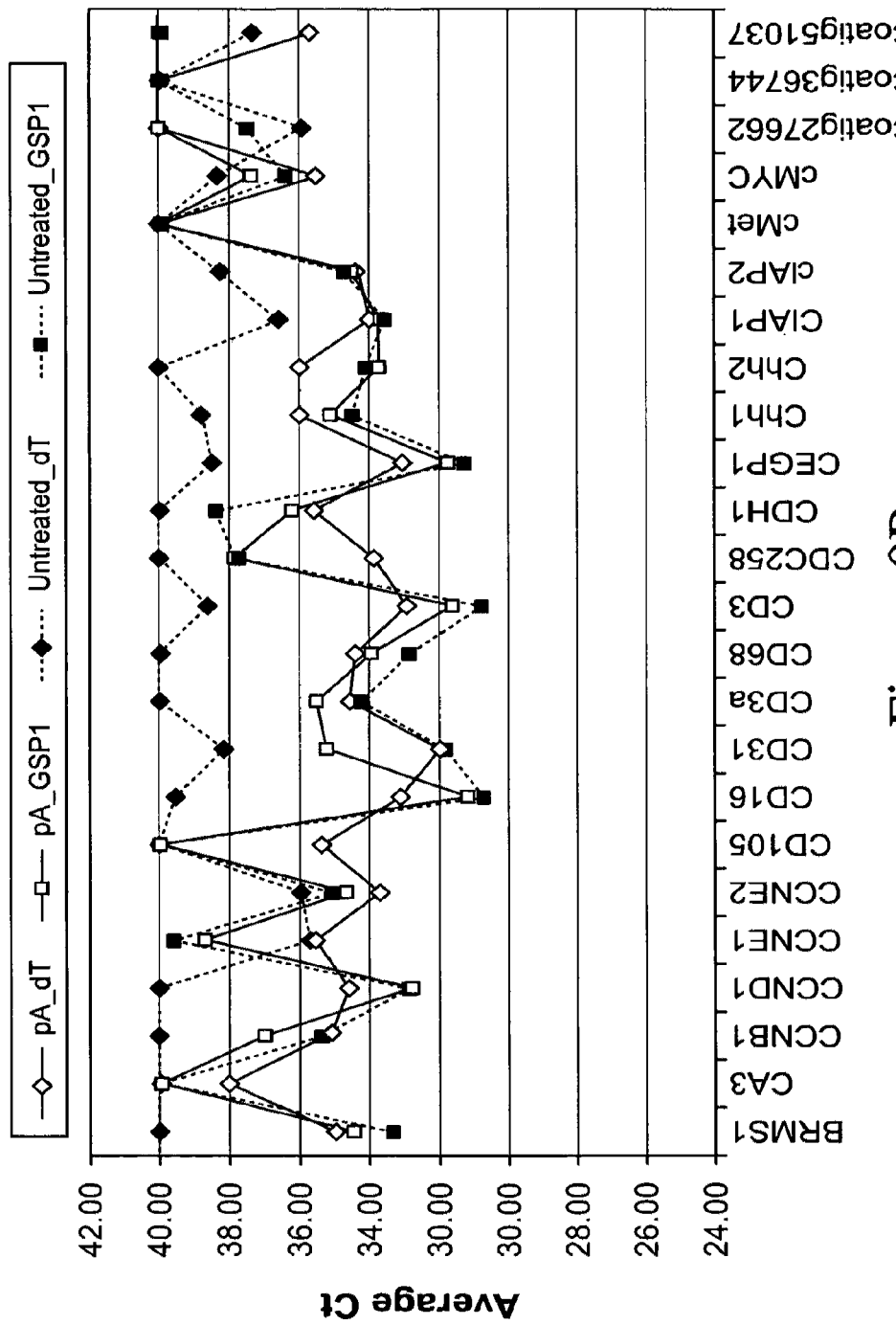
Figure 9C:
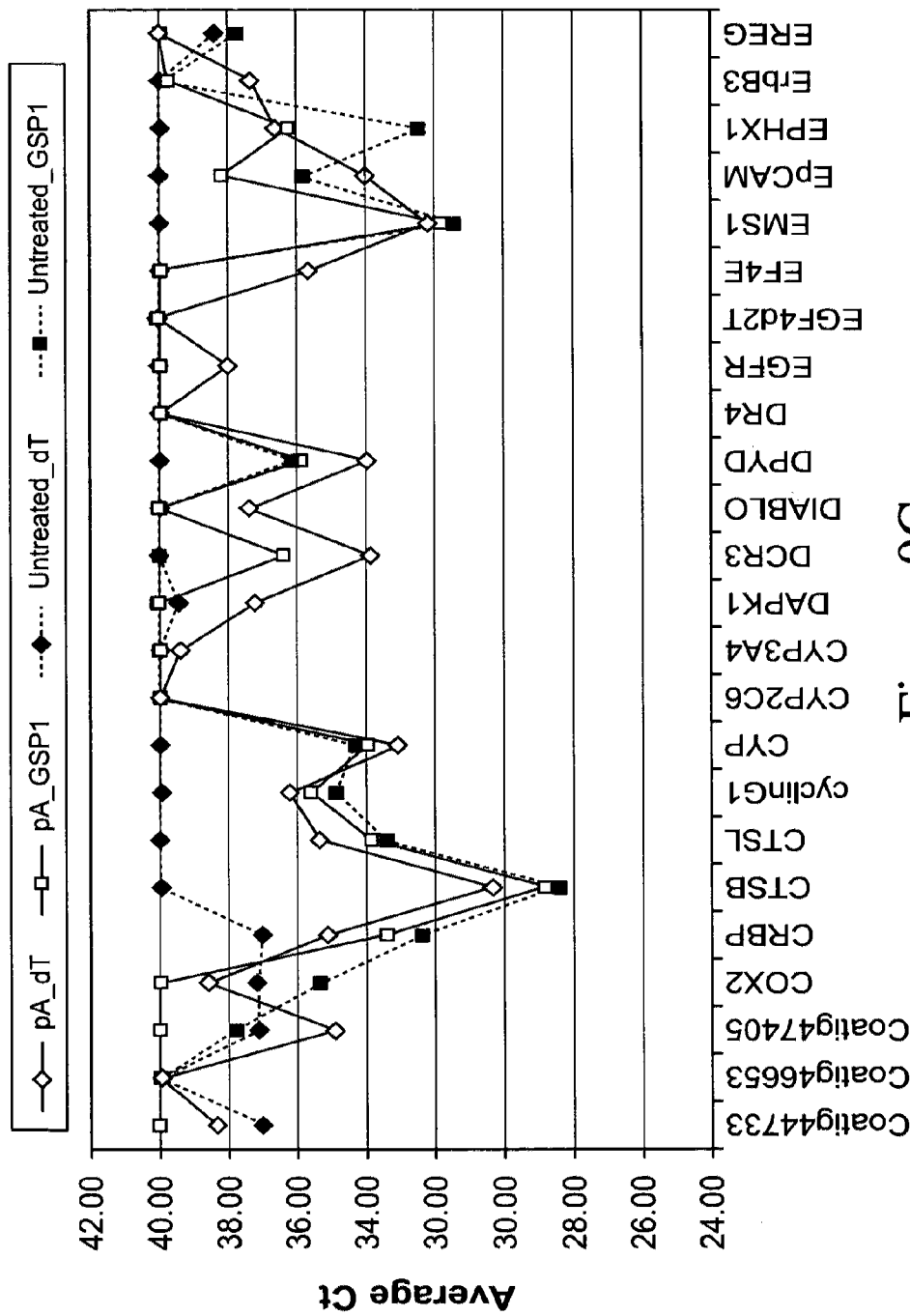
Figure 9D:
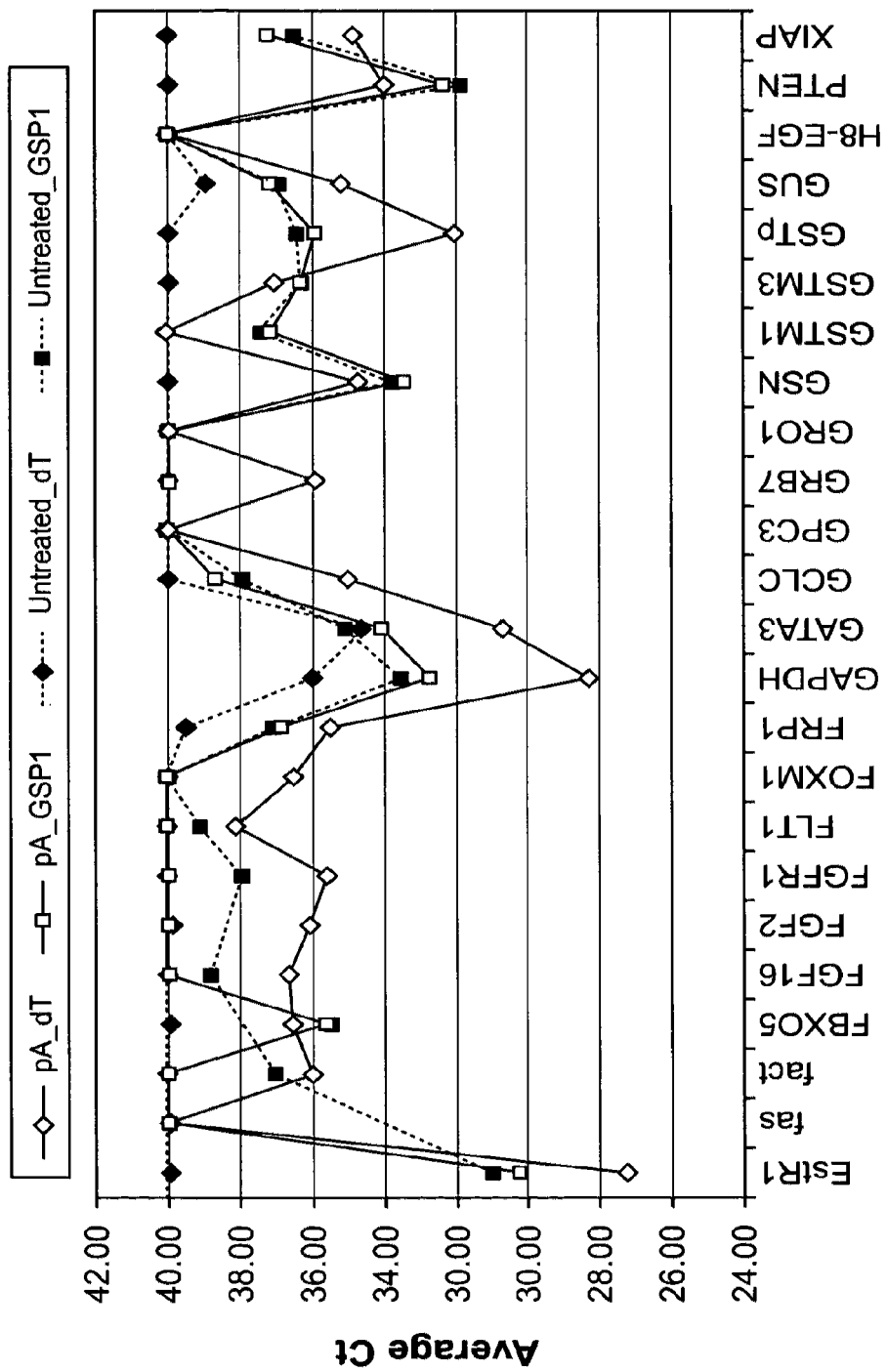

FIG. 8 shows selected gene expression analysis of breast tumor FPET RNA. Expression was analyzed by real time quantitative RT-PCR (TaqMan®) on an ABI Prism® 7700. Prior to gene expression analysis, the RNA was treated with CIP (+CIP) or buffer control (−CIP), followed by polyadenylation by EPAP. The RNA was then converted into cDNA with reverse transcriptase and oligo dT primers (+CIP/Oligo dT and −CIP/Oligo dT) or gene specific primers (+CIP/GSP and −CIP/GSP). Relative yields are measured by the threshold cycle (Ct). Inset: Agilent 2100 gel image of FPET RNA treated with CIP or buffer control followed by EPAP. Lane M shows RNA markers with the size of each band denoted in bases.

FIG. 9 shows a 96 gene panel expression analysis of breast tumor FPET RNA. Expression was analyzed by real time quantitative RT-PCR (TaqMan®) on an ABI Prism® 7900. Prior to gene expression analysis, the RNA was treated with PNK, followed by treatment with EPAP. The RNAs were then converted into cDNA with reverse transcriptase and oligo dT primers (pA_dT) or gene specific primers (pA_GSP1). Non-polyadenylated RNA was also converted to cDNA as above (untreated_dT and untreated GSP1). Relative yields are measured by the threshold cycle (Ct). Statistical analysis of the results are shown in Table 1.

Figure 10A:
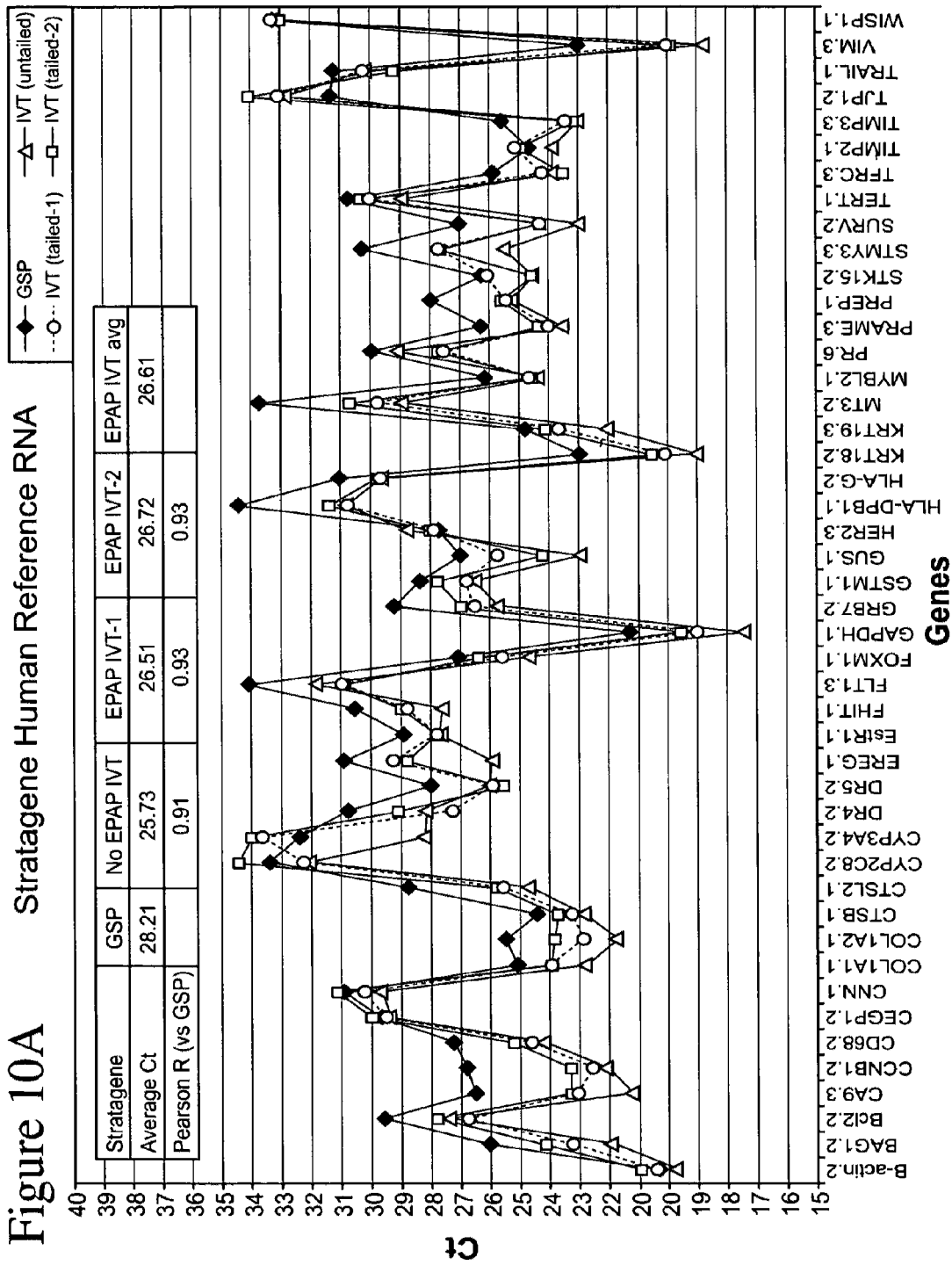
Figure 10B:
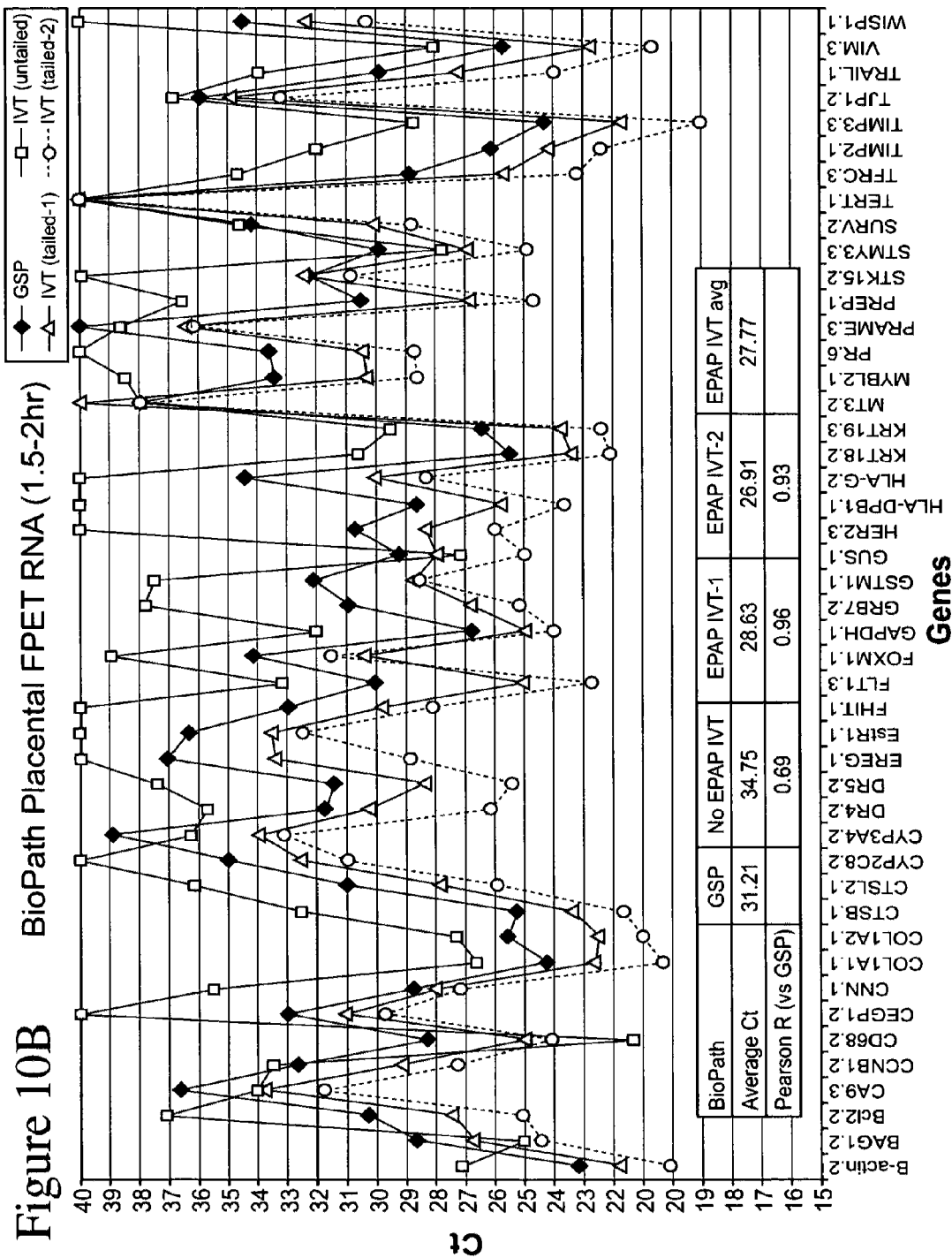
Figure 10C:
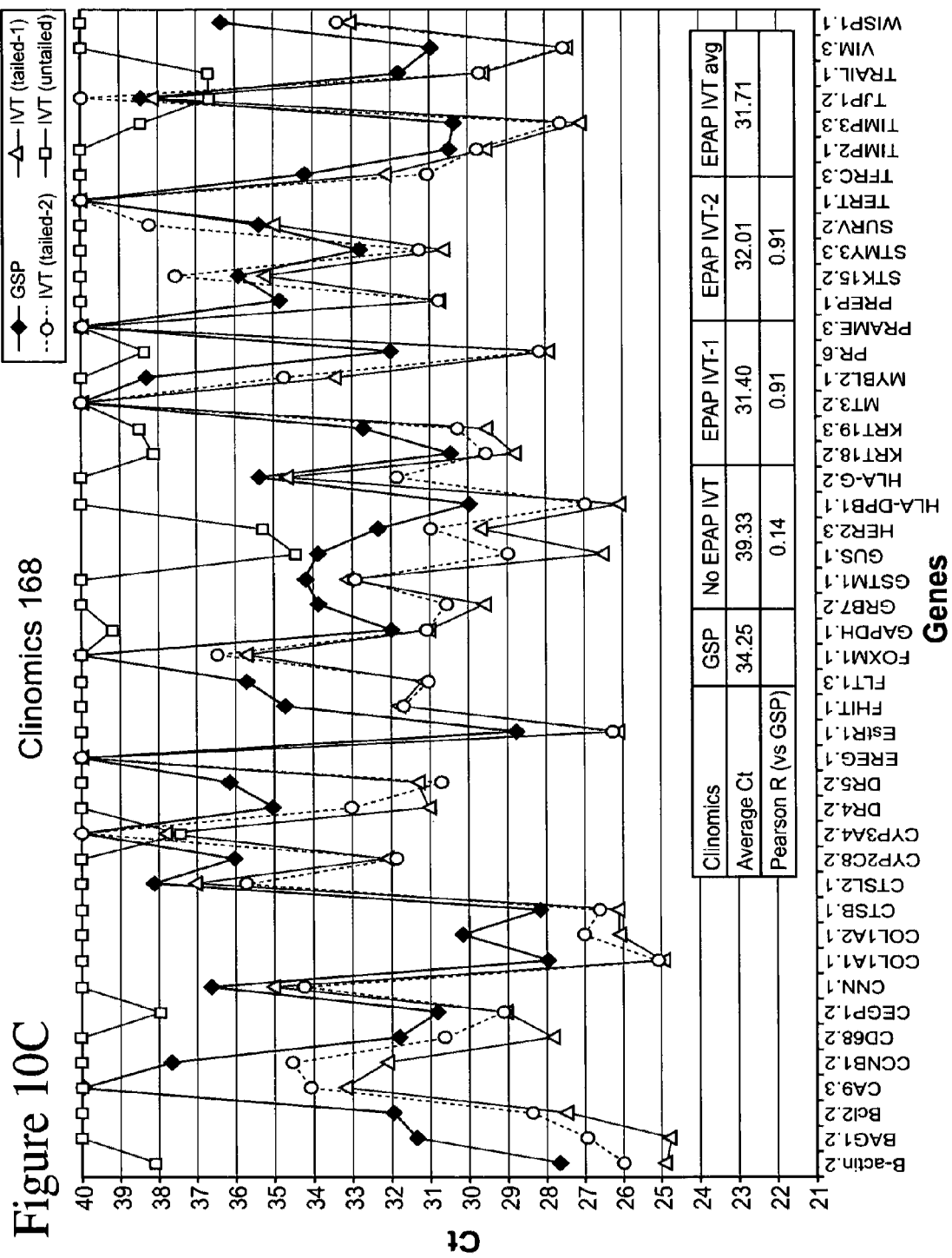

FIGS. 10 A-C show a 46 gene panel expression analysis of amplified and unamplified FPET RNA. Three different RNAs were profiled. Intact Universal total RNA (Stratagene, La Jolla, Calif.) is shown in FIG. 10A, placental FPET RNA (from placenta treated for 1.5-2 h with formalin and paraffin-embedded by BioPathology Sciences Medical Corporation, South San Francisco, Calif.) is shown in FIG. 10B and breast tumor FPET RNA (Clinomics BioSciences, Pittsfield, Mass.) is shown in FIG. 10C. Expression was analyzed by real time quantitative RT-PCR (TaqMan®) on an ABI Prism® 7900. Prior to gene expression analysis, two separate samples of RNA were treated with PNK followed by EPAP and then converted into cDNA with reverse transcriptase and oligo dT-T7 primers. The cDNA was made double-stranded with DNA polymerase I and RNAseH, amplified by IVT [IVT (tailed-1) and IVT (tailed-2)] and then analyzed by TaqMan® As a control, non PNK/nonEPAP-treated FPET RNA was converted to double-stranded cDNA and amplified by IVT [IVT (untailed)] as above or converted to cDNA by GSPs (GSP) prior to analysis by TaqMan.® Relative yields are measured by the threshold cycle (Ct). The inset tables show the overall average Ct of the 46 genes profiled for each RNA sample. Also shown are the Pearson correlation coefficients (R) between the unamplified (GSP) and amplified (IVT) RNA samples for the 46 profiled genes.

Figure 11:
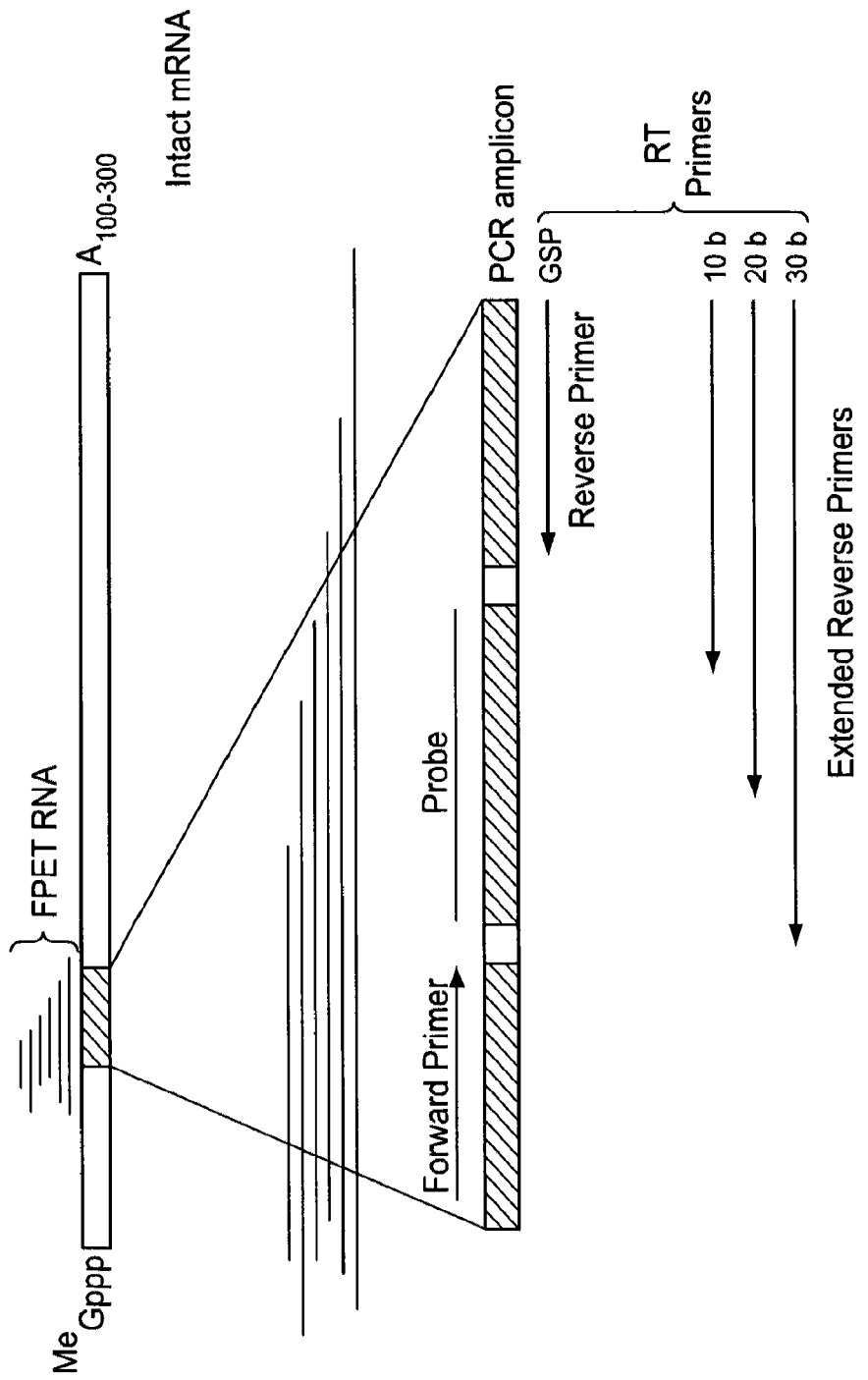

FIG. 11 is a scheme depicting the strategy for enhancing gene specific priming of fragmented FPET RNA. In this Figure, FPET stands for "fixed paraffin-embedded tissue, $^{Me}$Gppp refers to the 5' methylated guanylate CAP structure of mRNA, $A_{100-300}$ refers to the 3' polyA tract of mRNA, RT stands for reverse transcriptase, PCR stands for polymerase chain reaction, amplicon stands for the region of the mRNA amplified by PCR and GSP stands for gene specific primer. The extended reverse primers (10b, 20b and 30b) are identical to the reverse primer but extend roughly 10, 20 and 30 bases further into the amplicon. The 3' of the 30b RT primer and the 3' end of the forward primer are separated by a single base.

Figure 12:
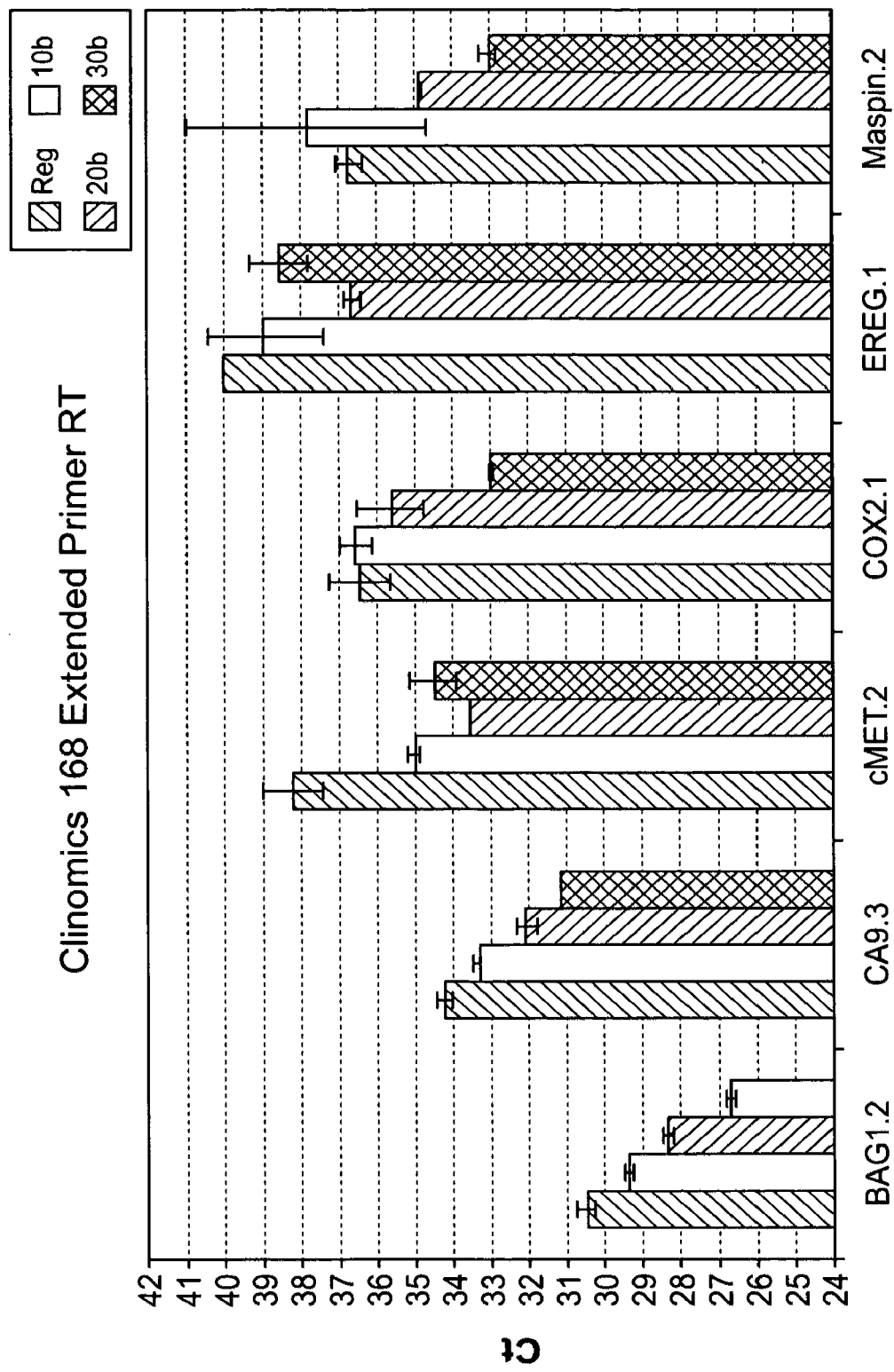

FIG. 12 shows selected gene expression analysis of breast tumor FPET RNA (Clinomics 168). Expression was analyzed by real time quantitative RT-PCR (TaqMan®) on an ABI Prism® 7700. cDNA synthesis was primed with either gene specific primers (Std primers) or extended reverse primers (10b, 20b and 30b primers). Relative yields are measured by the threshold cycle (Ct).

Figure 13:
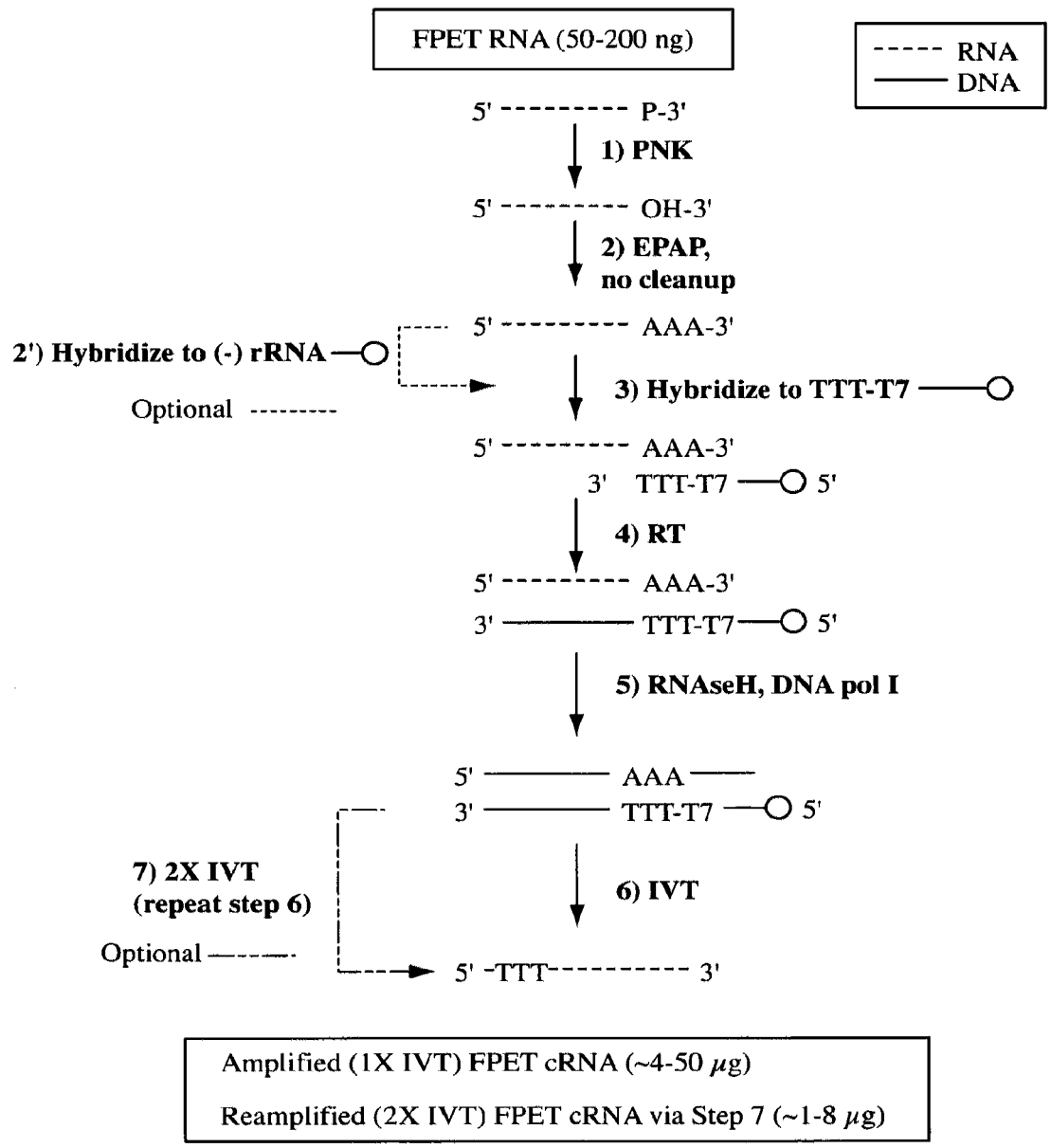

FIG. 13 is a schematic diagram illustrating the overall workflow of the improved, bead based amplification process in the invention used for measuring gene expression. In this figure, FPET stands for "fixed paraffin-embedded tissue, PNK stands for "polynucleotide kinase", EPAP stands for "*E. coli* polyA polymerase", O-T7-(TTT) is a solid phase, immobilized primer for cDNA synthesis consisting of a T7 RNA polymerase promoter sequence and an oligodeoxythymidylate sequence attached to a magnetic polystyrene bead, RT stands for "Reverse Transcriptase", RNAse H stands for "Ribonuclease H", DNA pol I stands for the "DNA polymerase I", IVT stands for "in vitro transcription", cRNA stands for "complementary RNA generated by IVT, and O-(−) rRNA refers to bead immobilized complementary ribosomal RNA sequences (synthesized as short DNA oligos). The improved, bead based protocol is shown in the central portion of the diagram (solid arrows). The process starts with FPET RNA, generally 50-200 ng, and involves 1) unblocking of the 3'OH on the terminal nucleotide with PNK, 2) direct EPAP poly A tailing of the FPET RNA 3' without cleanup from PNK step, 3) hybridization of polyadenylated FPET RNA to oligo dT-T7 RNA polymerase promoter sequences immobilized to beads followed by 4) cDNA synthesis with RT, 5) partial RNA degradation by RNAse H and second strand DNA synthesis with DNA polymerase I and 6) RNA amplification by in vitro transcription. An optional procedure for a second round of IVT is shown in step 7 (broken arrows). Another optional step, shown in step 2' involves depletion of ribosomal rRNA fragments (dotted arrow).

Figure 14:
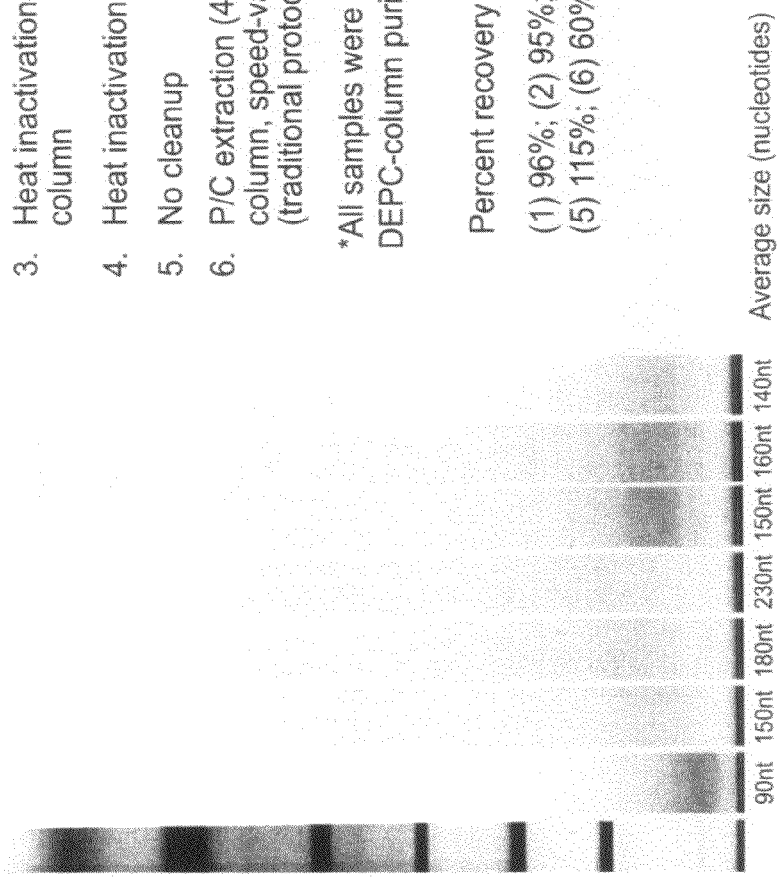

FIG. 14 shows the results from various PNK cleanup modifications followed by polyadenylation by EPAP. The left panel shows FPET RNA size by microcapillary electrophoresis using the Agilent 2100 Bioanalyzer. Lane descriptions: Ladder, RNA molecular weight markers from 200 bases (lowest) to 6000 bases; SM, unmodified FPET RNA. 1-6, PNK cleanup conditions described in the right panel. P/C refers to phenol/chloroform; DEPC-30 column refers to CHROMA SPIN™ DEPC-$H_2$O 30 column, heat inactivation conditions were 65° C., 20 min. Percent recovery after EPAP cleanup is relative to input FPET RNA (1000 ng).

Figure 15:
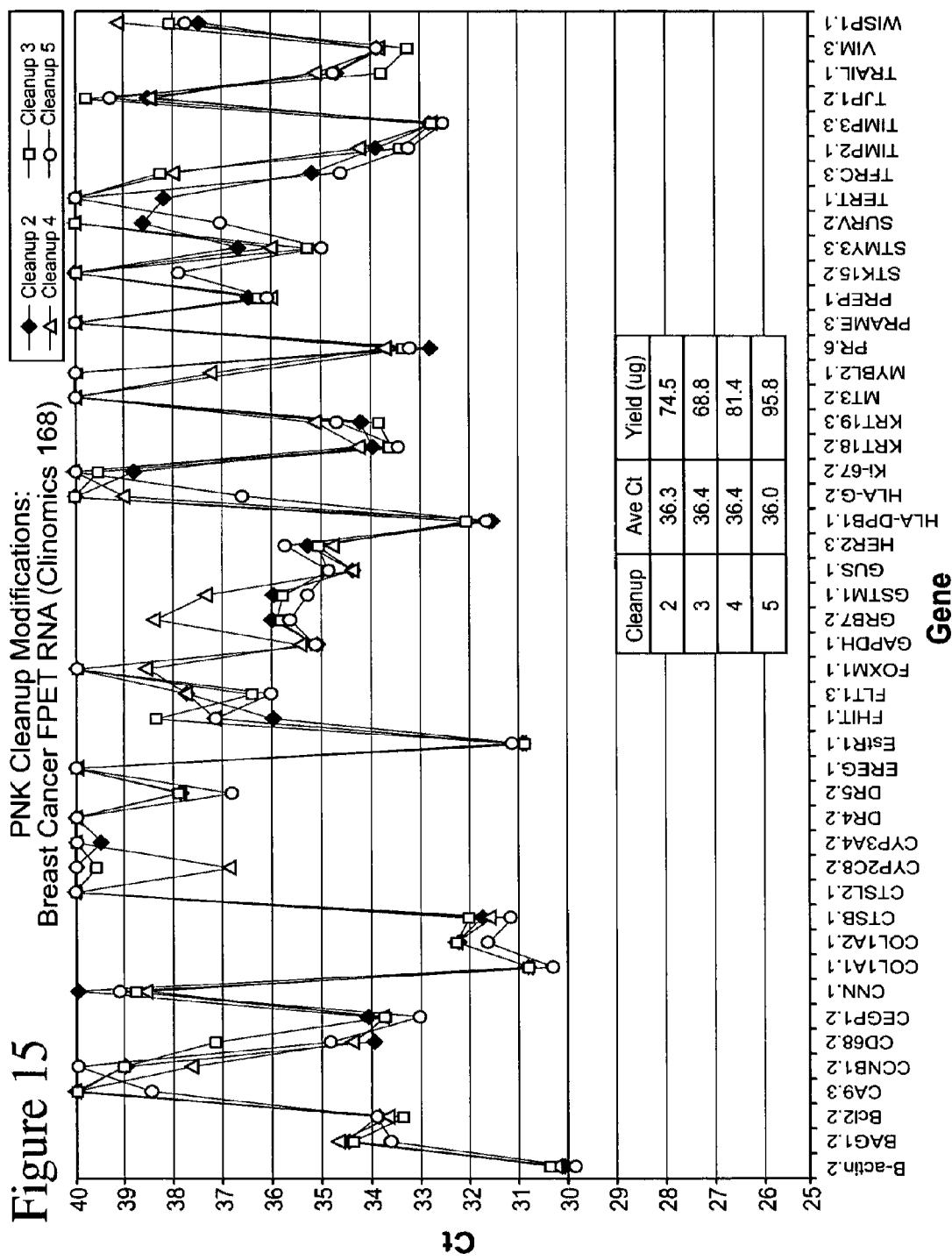

FIG. 15 shows a 47 gene panel expression analysis of amplified breast tumor FPET RNA (Clinomics BioSciences, Pittsfield, Mass.). Expression was analyzed by real time quantitative RT-PCR (TaqMan®) on an ABI Prism® 7900. Relative yields are measured by the threshold cycle (Ct). The inset tables show the overall average Ct of the 47 genes profiled for each cleanup condition and the cRNA yield for each IVT. The cleanup conditions are described below in Example 2.

Figure 17A:
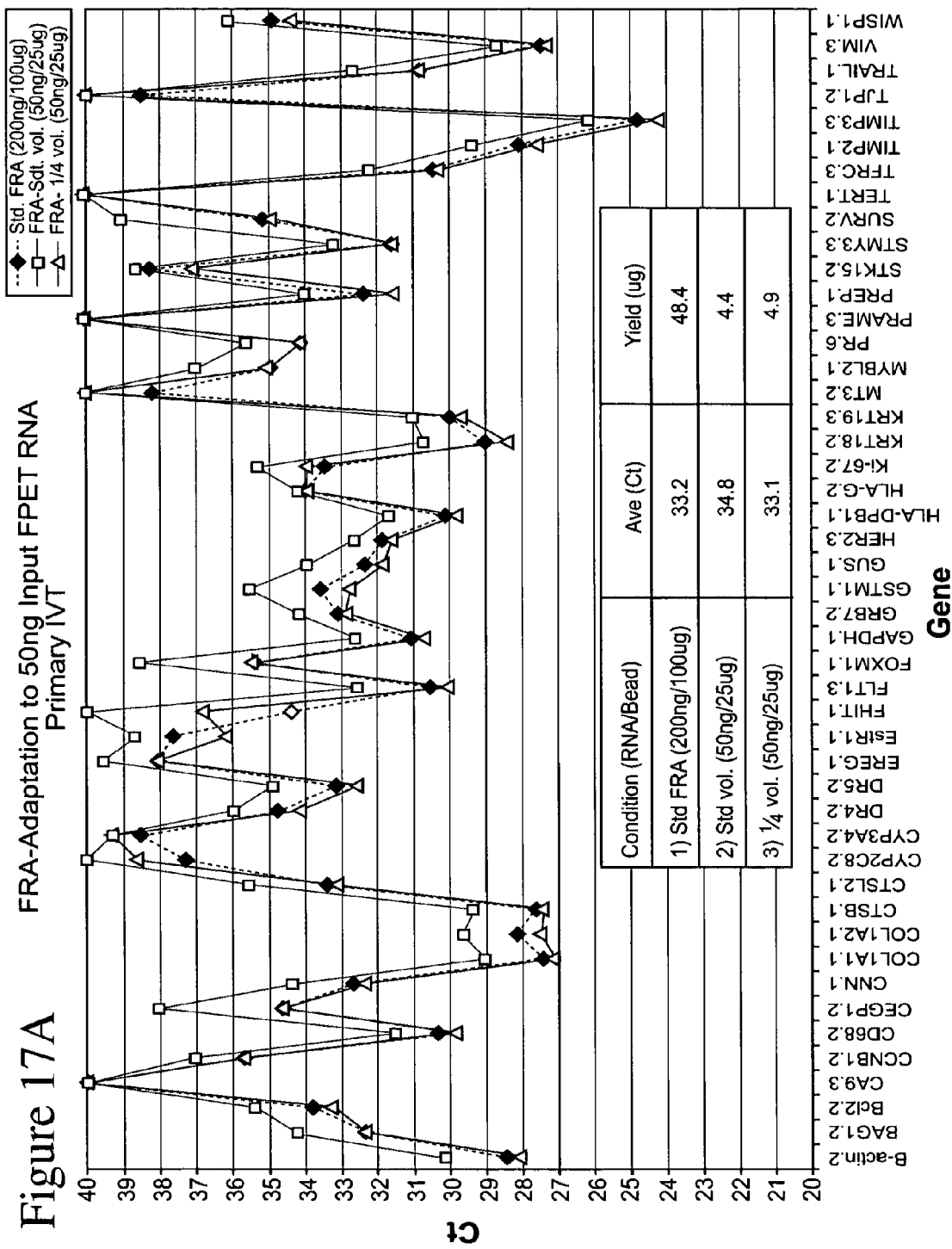
Figure 17B:
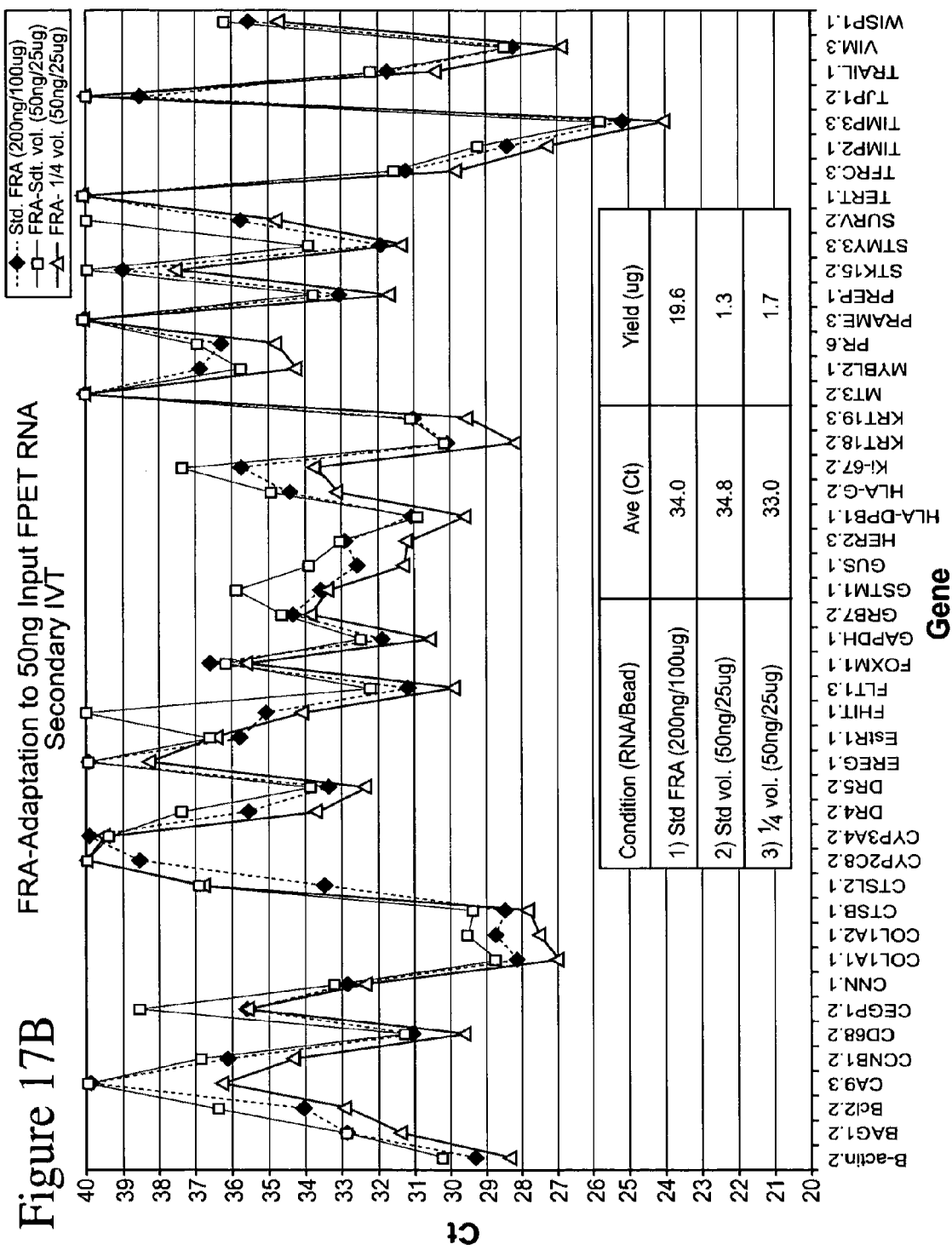
Figure 17C:
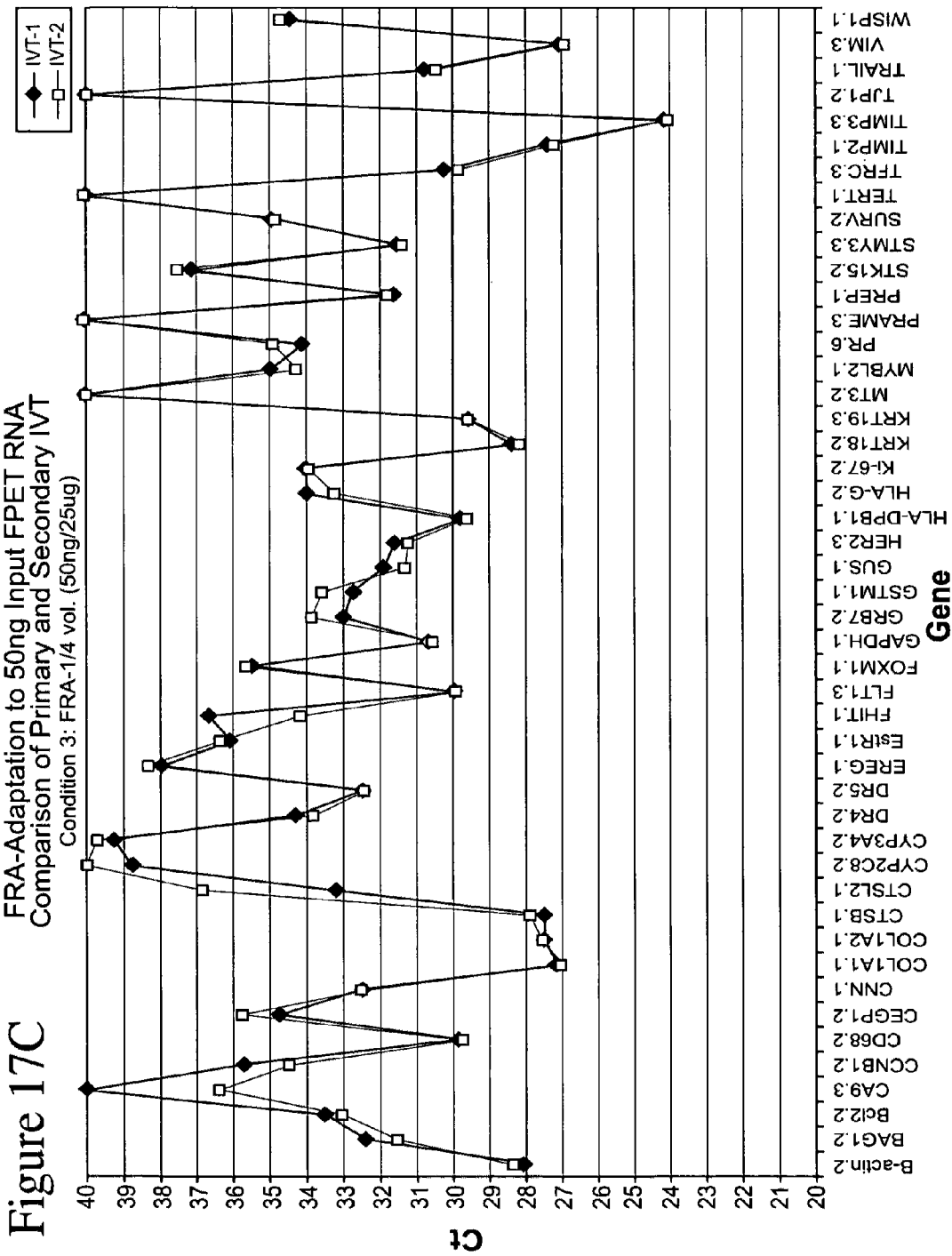

FIG. 16 shows a 47 gene panel expression analysis of Placental FPET RNA amplified by a non-bead based (Free IVT) and a bead based (Solid Phase IVT) described in Example 3. For comparison, the profile of unamplified starting material (SM) is also shown. The placenta was treated for 1.5-2 h with formalin and paraffin-embedded by BioPathology Sciences Medical Corporation, South San Francisco, Calif. Expression was analyzed by real time quantitative RT-PCR (TaqMan®) on an ABI Prism® 7900. Relative yields are measured by the threshold cycle (Ct). The inset tables show the overall average Ct of the 47 genes profiled for each cleanup condition and the cRNA yield for each IVT. Also shown are yields after normalization (Yield; Ct. adj.). The equation for normalizing yields is: cRNA Yield/$2^{(Avg.Ct.-SM\ Ct.)}$ FIGS. 17A-C show a 47 gene panel expression analysis of amplified Placental FPET RNA. The placenta was treated for 1.5-2 h with formalin and paraffin-embedded by BioPathology Sciences Medical Corporation, South San Francisco, Calif. Expression was analyzed by real time quantitative RT-PCR (TaqMan®) on an ABI Prism® 7900. Relative yields are measured by the threshold cycle (Ct). The inset tables show the overall average Ct of the 47 genes profiled for each FRA condition and the cRNA yield for each IVT. The three FRA conditions are described below in Example 4. FIGS. 17A and 17B show the results from the primary and secondary amplification, respectively. FIG. 17C shows a comparison of a primary and secondary IVT (Condition 3).

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), provide one skilled in the art with a general guide to many of the terms used in the present application.

The term "polyadenylation" or "poly A tailing" refers to the addition of a stretch of adenylate molecules (poly (A)) to the 3' end of RNA, e.g. mRNA.

"Efficiency of polyadenylation" refers to the ease with which poly A addition occurs and is dependent upon the availability of the free 3'-hydroxyl (3' OH) group at the 3'-terminal ribose moiety of RNA.

"Blocking of polyadenylation" or "blocked 3'end" of RNA refers to blocking the availability of the 3'-terminal ribose moiety of RNA for a polyadenylation reaction. This may occur, for example, because the 3' terminus of RNA contains various phosphate esters typically 2'-3' cyclic phosphates, 2'-monophosphates and 3'-monophosphates which need to be removed to permit addition of a poly A tail to the 3' terminus of the RNA.

"Dephosphorylation" refers to the removal of phosphate esters (described above) by any methods, including but not limited to enzymatic techniques, such as using calf intestinal phosphatase (CIP) or T4 Polynucleotide Kinase (PNK).

"Threshold cycle (Ct)" refers to relative yields of nucleic acid amplified in a PCR reaction. During TaqMan PCR, the 5'-nuclease activity of the Taq polymerase is utilized to cleave and release a quenched reporter dye present on a third oligonucleotide primer (which is non-extendible by Taq polymerase) that detects a nucleotide sequence located between the two PCR primers. One molecule of reporter dye is liberated for each newly synthesized nucleic acid molecule and detection of this unquenched reporter dye provides the basis for quantitative interpretation of amplification or the mount of product amplified to that point in the amplification reaction. The point when the fluorescent signal is first recorded as statistically significant is the threshold cycle (Ct). The lower the Ct value, the more abundant the mRNA is and the better the performance of the nucleic acid (cDNA or poly A mRNA or degraded mRNA) in the expression profiling array.

The term "microarray" refers to an ordered arrangement of hybridizable array elements, such as polynucleotide probes, on a substrate.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes, or a comparison of the ratios of the expression between two or more genes, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least about two-fold, preferably at least about four-fold, more preferably at least about six-fold, most preferably at least about ten-fold difference between the expression of a given gene in normal and diseased subjects, or in various stages of disease development in a diseased subject.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B. Lewin. Genes IV Cell Press, Cambridge Mass. 1990). In theory the term "intron" refers to any segment of DNA that is transcribed but removed from within the transcript by splicing together the exons on either side of it. Operationally, exon sequences occur in the mRNA sequence of a gene as defined by Ref. Seq ID numbers. Operationally, intron sequences are the intervening sequences within the genomic DNA of a gene, bracketed by exon sequences and having GT and AG splice consensus sequences at their 5' and 3' boundaries.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994). Specific protocols are described in the Materials and Method section of the Example below.

As discussed earlier, gene expression profiling has become an important tool of biological research and clinical practice.

Real-Time Reverse Transcriptase PCR (RT-PCR)

Of the gene expression profiling techniques, the most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MMLV-RT). The reverse transcription step is typically primed using gene specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or The polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real-time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

Microarray Analysis

Often another method of choice for gene expression profiling is the microarray technique. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of n-tRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

RNA Extraction and Amplification for Gene Expression Profiling

A common step in gene expression profiling by the RT-PCR and microarray techniques is the extraction of mRNA from biological samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include Masterpure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

If necessary, DNA can be removed at various stages of RNA isolation, by DNase or other techniques well known in the art. After analysis of the RNA concentration after purification, RNA repair and/or amplification steps may be necessary before subjecting the RNA to any known expression gene profiling methods, including RT-PCR coupled with 5' exonuclease of reporter probes (TaqMan® type assays), flap endonuclease assays (Cleavase and Invader type assays), oligonucleotide hybridization arrays, cDNA hybridization arrays, oligonucleotide ligation assays, 3' single nucleotide extension assays and other assays designed to assess the abundance of specific mRNA sequences in a biological sample.

Figure 2:
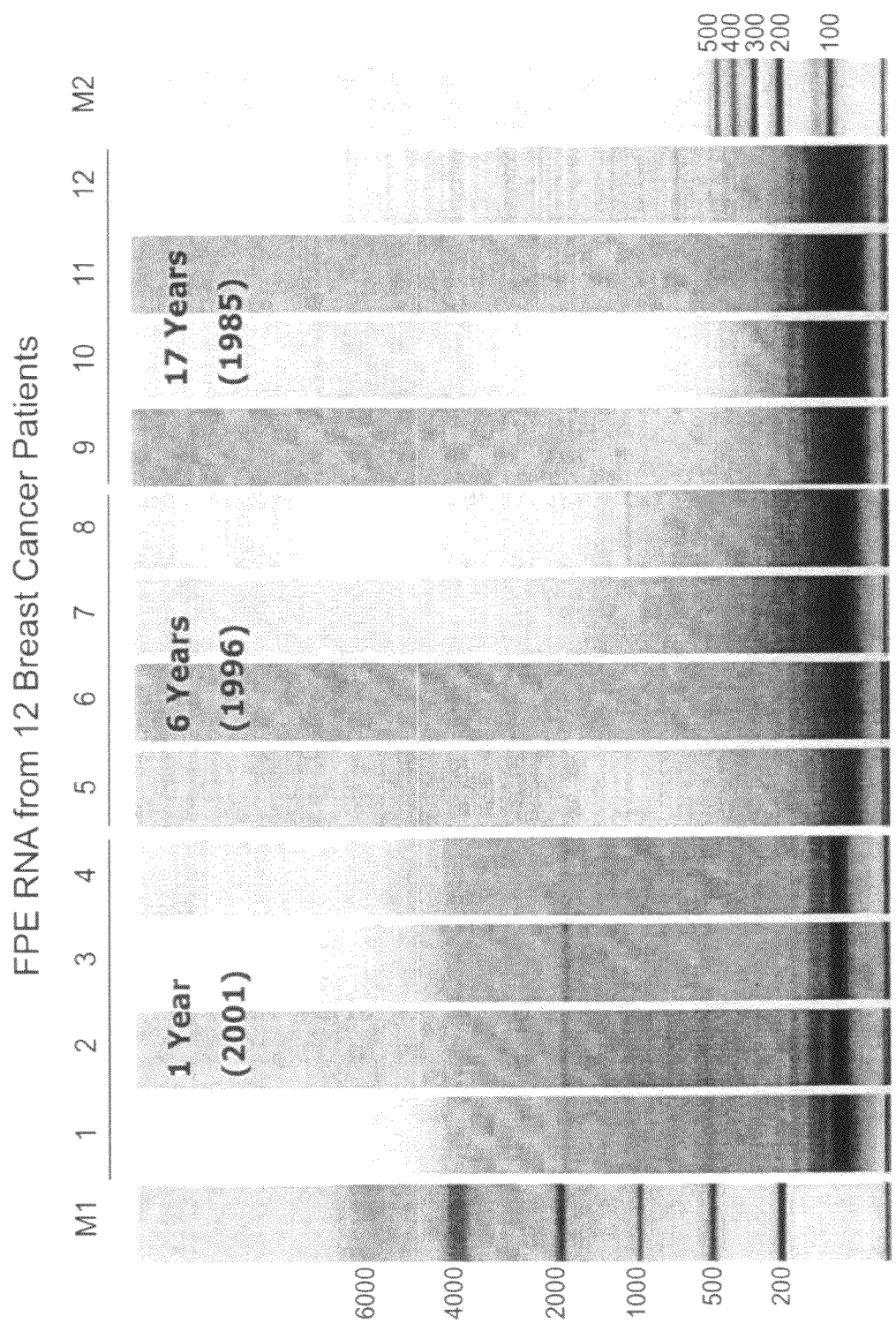
FIG. 2 shows a gel image of FPET RNA isolated from twelve different breast cancer patient's biopsies. Lanes M1 and M2 show RNA markers with the size of each band denoted in bases. Lanes 1-4, 5-8 and 9-12 are from tumor biopsies that have been archived for 1, 6 and 17 years respectively. Samples were analyzed by capillary electrophoresis on an Agilent 2100 Bioanalyzer using an RNA 6000 Nanochip.

Despite the availability of commercial products, and the extensive knowledge available concerning the isolation of RNA from tissues, isolation of nucleic acid (RNA) from fixed, paraffin-embedded tissue specimens (FPET) and its use for gene expression profiling is not without difficulty.

mRNA is notoriously difficult to extract and maintain in its native state, consequently, mRNA recovered from various biological sources, and specifically from archived, fixed paraffin-embedded tissue (FPET) is often fragmented and/or degraded. FIG. 2 shows an example of RNA isolated from formalin-fixed, paraffin embedded (PFE) breast cancer samples that were archived from 1 to 17 years. RNA degradation progresses with archive storage time and results in RNA having an average size of about 100 bases after 17 years of storage. By comparison, intact mRNA has an average size of about 1800-2000 bases.

As discussed above, the extraction of mRNA is typically followed by conversion to cDNA using the primer dependent enzyme reverse transcriptase (RT). Universal conversion of intact mRNA to cDNA is performed efficiently by oligo dT priming of the mRNA in the presence of RT.

Figure 3:
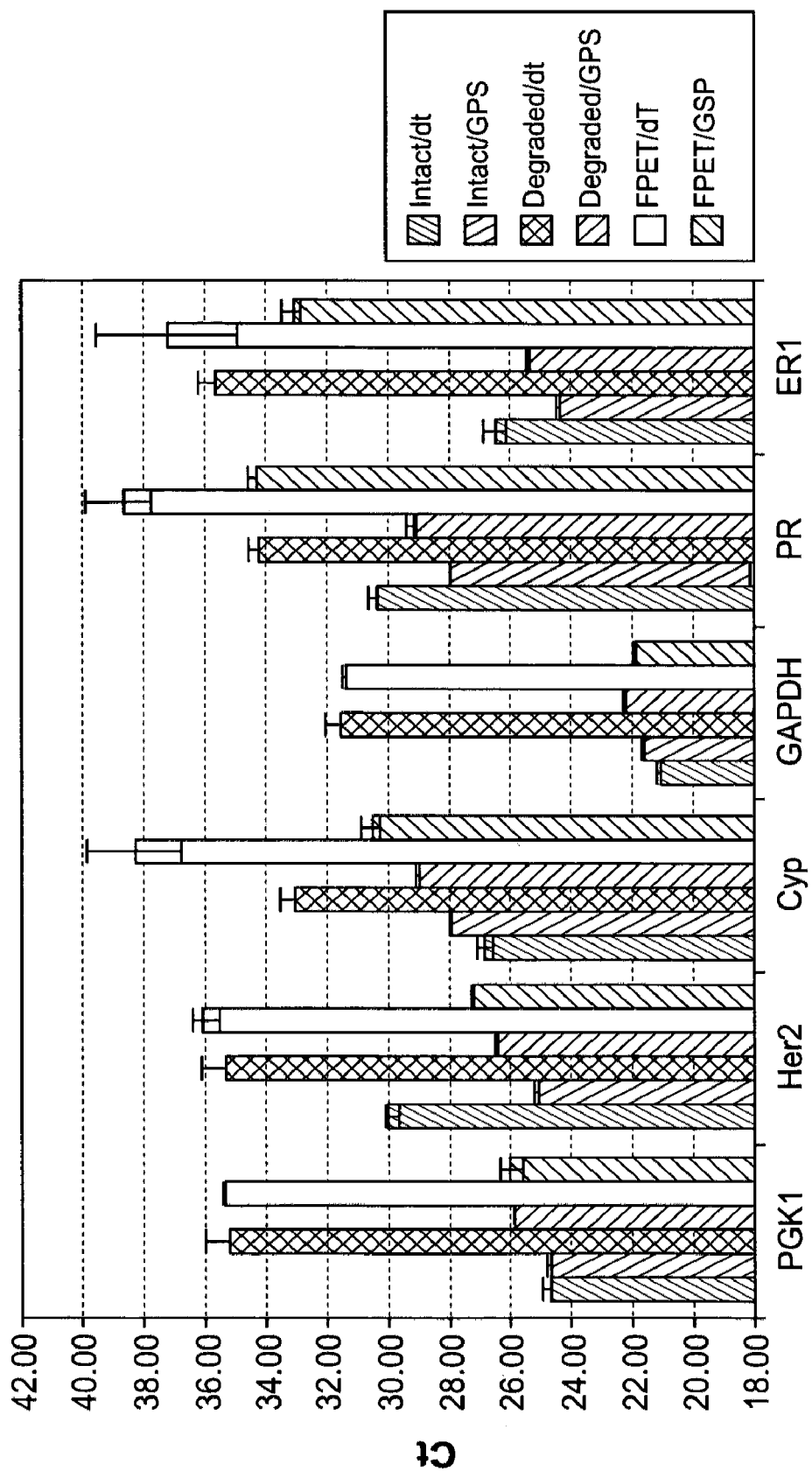
FIG. 3 shows selected gene expression analysis of breast tumor FPET RNA, randomly degraded breast tumor RNA and intact breast tumor RNA. Expression was analyzed by real time quantitative RT-PCR (TaqMan®) on an ABI Prism® 7700. cDNA synthesis was primed with either gene specific primers (GSP) or oligo $(dT)_{12-18}$. Relative yields are measured by the threshold cycle (Ct).

Effective priming with oligo dT during the PCR reaction is made possible by the presence of a poly A tract at the 3' end of mRNA. FIG. 3 shows that intact mRNA can be efficiently profiled by TaqMan analysis using cDNA generated by RT and oligo dT priming. As can also be seen, profiling of fixed, paraffin-embedded (FPET) or randomly degraded RNA (obtained by alkaline hydrolysis) by oligo dT primed cDNA synthesis is extremely inefficient as judged by the lower TaqMan signal (higher Ct) obtained relative to intact RNA. For the genes profiled, the signals from the intact RNA are on the average 500-1000-times greater than the corresponding signals from FPET RNA.

The present inventors have considered that inefficient conversion of FPET mRNA to cDNA by oligo dT priming might result from the fact that the majority of the degraded mRNAs does not contain a polyA tail. Importantly, FIG. 3 also shows that degraded RNA can be efficiently profiled using gene-specific primers (GSP). This indicates that most regions of the expressed genes are present in the randomly fragmented RNA in proportions expected for the intact mRNA. This result suggests that it should be possible to perform effective universal gene expression profiling on fragmented, e.g. FPET mRNA extracts.

Figure 4:
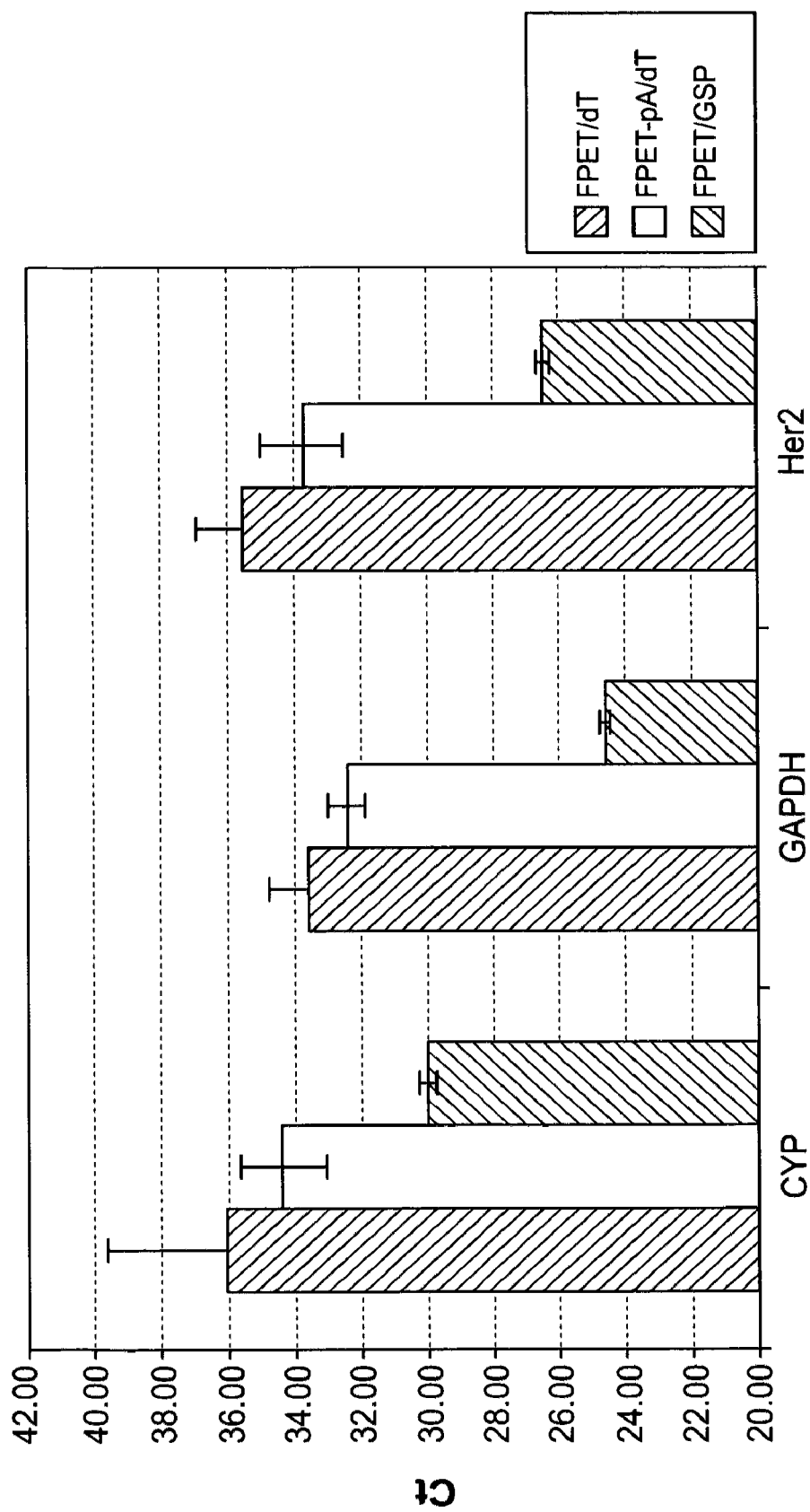
FIG. 4 shows a selected gene expression analysis of breast tumor FPET RNA. Expression was analyzed by real time quantitative RT-PCR (TaqMan®) on an ABI Prism® 7700. cDNA synthesis was primed with either GSPs or oligo $(dT)_{12-18}$ using template RNA that was not polyadenylated (FPET/GSP and FPET/dT) or cDNA synthesis was primed with oligo $(dT)_{12-18}$ using template RNA that was polyadenylated (FPET-pA/dT). Relative yields are measured by the threshold cycle (Ct).

To this end, it has been attempted to globally reverse transcribe FPET RNA by first polyadenylating the RNA and then performing oligo dT primed RT. As shown in FIG. 4, polyadenylation of FPET RNA prior to oligo dT priming increased the conversion of the RNA to cDNA by about 2-4-fold as judged by TaqMan analysis of 3 mRNAs. This result has been interpreted to suggest that polyadenylation may be a useful method to prepare fragmented, e.g. FPET RNA for global reverse transcription and subsequent gene expression profiling. However, this signal amplification was still only a small fraction of that obtained by priming with gene specific primers (GSP), which is the most efficient currently used method of priming the conversion of selected regions of mRNA to cDNA by RT.

One recognition underlying the present invention is that the limited conversion of fragmented RNA to cDNA is due to the fact that in fragmented RNA, the 3' end of a large proportion of RNA fragments is blocked and therefore not accessible to polyadenylation.

Figure 5:
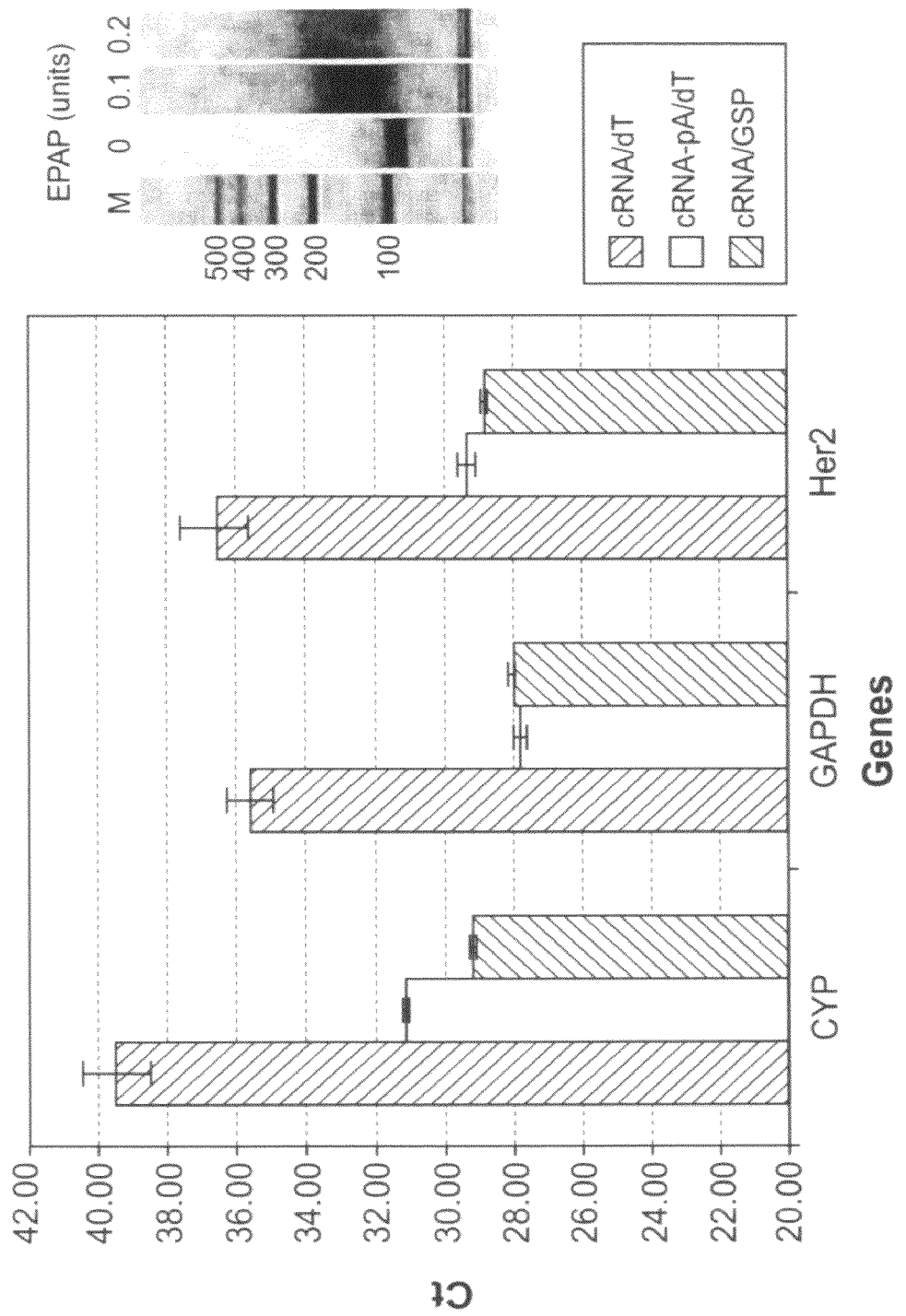
FIG. 5 shows a gene expression analysis of in vitro transcribed cRNAs. Expression was analyzed by real time quantitative RT-PCR (TaqMan®) on an ABI Prism® 7700. RNA polyadenylation was performed with 0.2 units of EPAP and cDNA synthesis was performed as in FIG. 4. See Materials and Methods for generating the template cRNA. Relative yields are measured by the threshold cycle (Ct). Inset: Agilent 2100 gel image of cRNAs treated with 0, 0.1 or 0.2 units of EPAP. Lane M shows RNA markers with the size of each band denoted in bases.

A model system has been developed to monitor the level of polyadenylation of fragmented, e.g. FPET RNA and determine its effect on gene expression profiling when RNA 3' ends are not blocked. RNA fragments (~100 bases) of three genes were generated by in vitro transcription (IVT), then pooled and polyadenylated. Polyadenylation was monitored by capillary electrophoresis on the Agilent 2100 BioAnalyzer. The FIG. 5 inset demonstrates that tailing of RNA with 0.1 and 0.2 units of E. coli polyA polymerase (EPAP) adds between 20 and 200 adenylates to the RNA. The polyadenylated RNA was then reverse transcribed to cDNA using oligo dT priming and assayed by TaqMan analysis (FIG. 5). As can be seen, polyadenylation of the RNA (0.2 EPAP/oligo-dT) resulted in a dramatic increase in TaqMan signal relative to non-tailed RNA.

Based on the above result, it has been hypothesized that most 3' ends in the fragmented FPET RNA were blocked, probably due to enzymatic hydrolysis with cellular RNAses that commonly yield 3' $PO_4$ or cyclic 2'-3' $PO_4$. These modifications would effectively block the polyadenylation of FPET RNA.

According to a variation of the method of the invention, effective conversion of fragmented mRNA to cDNA starts with the unblocking of the 3' terminus of the RNA. Any phosphatase, like calf alkaline phosphatase (CIP) or T4 polynucleotide kinase (PNK) can be used to remove 2'-3' cyclic phosphates, 2'-monophosphates and 3'-monophosphates, generated typically on the 3' terminal ribose moiety of degraded RNAs. This ensures efficient poly A addition by poly A polymerase to the 3' terminus of the FPET RNA. PNK, which is also a 3' phosphatase, catalyzes the hydrolysis of 3'-phosphoryl groups of deoxynucleoside 3'-monophosphates, deoxynucleoside 3'-, 5'diphosphates and of 3'-phosphoryl-polynucleotides. Other phosphatases like bacterial alkaline phosphatase, shrimp alkaline phosphatase, and derivatives thereof, can also be used to carry out such dephosphorylation reactions. The 3' terminus now has a free 3'OH available.

Polyadenylation or "poly A tailing" of mRNA or FPET mRNA after enzymatic reactions like dephosphorylation involves appending of adenylate molecules or poly (A) to the 3' OH end of the RNA. In one embodiment, this is done using E. coli poly A polymerase. However, as will be understood by those skilled in the art, other poly A polymerases can also be used.

Specific Embodiments

Figure 1:
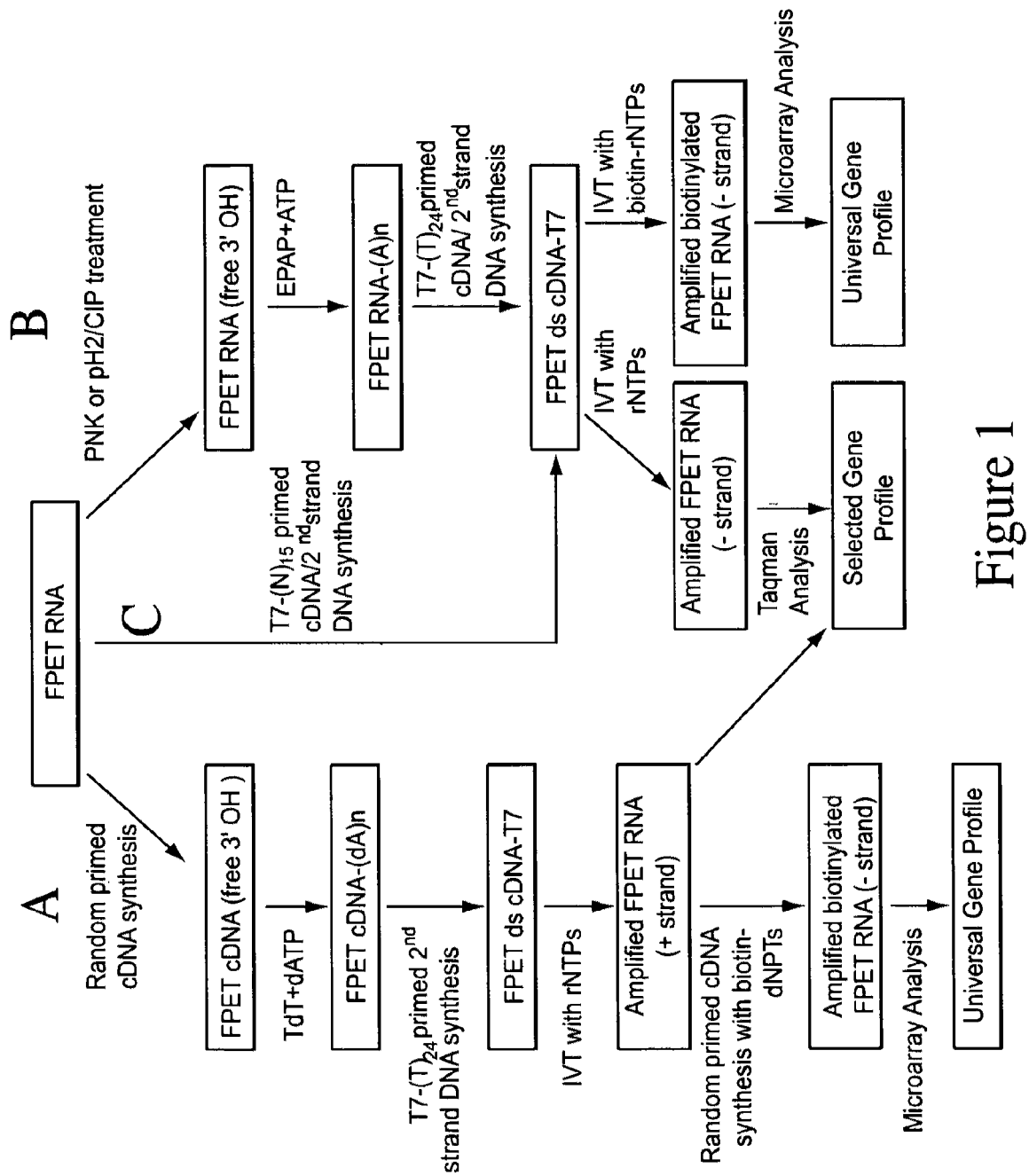
FIG. 1 is a chart illustrating the overall workflow of the amplification process in the invention used for measuring gene expression. In this Figure, FPET stands for "fixed paraffin-embedded tissue, PNK stands for "polynucleotide kinase", CIP stands for "calf intestinal alkaline phosphatase", EPAP stands for "*E. coli* polyA polymerase", TdT stands for "Terminal Transferase", IVT stands for "in vitro transcription", rNTP stands for "ribonucleoside-5'-triphosphate", dNTP stands for "2'-deoxyribonucleoside-5'-triphosphate", ATP stands for "adenosine-5'-triphosphate". T7-$(T)_{24}$ is a primer for cDNA synthesis using reverse transcriptase and stands for T7 RNA polymerase promoter sequence attached to the 5' end of polydeoxyadenylate. T7-(N)15 is a primer for cDNA synthesis using reverse transcriptase and stands for T7 RNA polymerase promoter sequence attached to the 5' end of a random deoxy-pentadecamer.

Three representative protocols (A, B and C) of the invention are illustrated in FIG. 1. Processes A and B start with FPET RNA and involve 1) direct or indirect unblocking of the 3'OH on the terminal nucleotide, 2) poly A tailing of the 3' end, 3) poly dT-primed double-strand cDNA synthesis with the incorporation of a T7 RNA polymerase promoter, and 4) RNA amplification by in vitro transcription.

Process C (central arrow in the diagram) starts with FPET RNA and involves 1) T7-(N)15 primed double-stranded cDNA synthesis with the incorporation of a T7 RNA polymerase promoter, and 2) RNA amplification by in vitro transcription.

Specifically, Protocol A involves a random primed (hexamers) cDNA synthesis that generates cDNA with a free 3' OH on the terminal nucleotide of the FPET cDNA. The FPET cDNA is then tailed with Terminal Transferase (TdT) and dATP. The poly dA-tailed cDNA is then converted to double-stranded DNA with DNA polymerase I (Klenow) and T7-$(dT)_{24}$ primer. This material is then amplified with T7 RNA polymerase and rNTPs to generate FPET RNA (+strand). This material is suitable for gene expression analysis by Taq-Man®. In order to be a suitable target for microarrays containing (+) strand probes, the FPET RNA needs to be converted to (−) strand cDNA in the presence of biotinylated dNTPs, random primers and RT. This material is now suitable for hybridization to microarrays in order to perform universal gene expression profiling. For microarrays containing double-stranded probes, this final step is not necessary. In this case, the IVT step should include biotin-rNTP's as in protocol B (below).

Protocol B involves an unblocking of the 2' OH and/or 3'OH of the 3'-terminal nucleotide of FPET RNA with polynucleotide kinase (PNK) or [pH2 treatment (0.01M HCl or maleic acid)] followed by calf intestinal alkaline phosphatase (CIP). This enables the RNA to be efficiently polyadenylated at the 3' terminal nucleotide with E. coli polyA polymerase and ATP. Following polyadenylation, the RNA is converted to cDNA by reverse transcriptase using either oligo dT or oligo dT-T7 as primers. The oligo dT primed cDNA can be directly used for gene expression analysis by TaqMan® analysis. This method is preferred if the amount of the FPET RNA is not limiting. If the amount of the FPET RNA is limiting, then the preferred method is to use the oligo dT-T7 primed cDNA, convert it to double-stranded DNA with DNA polymerase I and RNAse H and subsequently amplify it with T7 RNA polymerase and rNTPs. If the sample is to be used for microarray analysis, then the oligo dT-T7 primed cDNA is converted to double-stranded DNA as above, and subsequently amplified with T7 RNA polymerase and biotinylated rNTPs. Again, this protocol allows universal gene expression profiling, using FPET RNA or, in a more general sense, fragmented RNA of any origin.

An additional protocol of the invention is shown in FIG. 11. In this protocol, the RT step is enhanced by using longer reverse primers as shown (10 bases, 20 bases and 30 bases) under otherwise normal RT conditions. The longer primers enable an increase in priming of the fragmented RNAs resulting in more cDNA target for the PCR step. In addition, the longer primers may aid in reverse transcription by bridging formalin-modified bases that would otherwise block enzymatic activity. An additional modification includes performing the initial two cycles of PCR at 50° C. This enables the amplification of more target cDNA due to the lower annealing temperature. Both of the above steps result in stronger gene expression signals.

Further embodiments, provide several additional improvements over the universal amplification of fragmented RNA protocol (FRA), as discussed above. These improved procedures enable global reverse transcription and amplification of smaller quantities (50 ng) of even highly fragmented FPET RNA samples in an automatable, solid phase bead format. The improvements also decrease the number of cleanups between enzymatic steps involved in the FRA discussed above, making the process a higher throughput procedure. Furthermore, the improvements permit the archiving of complete fragmented RNA transcriptomes on beads. Although fragmented, the archived RNAs are easily reamplified thus allowing reproducible measurement of mRNA levels of all expressed genes in biopsied or resected tumor tissue and archived paraffin-embedded tissue samples. Finally, the procedure can also easily incorporate an enrichment step for mRNA that allows increased sensitivity of gene expression analysis.

A rapid universal FPET RNA amplification procedure should greatly increase the number of genes that can be expression profiled and the number of studies that can be performed with typically limiting amounts of valuable clinical samples.

The specific improvements and changes to the basic protocol that are incorporated to create the improved bead based protocol are as follows:

(a) removal of the cleanup step between deblocking the 3' termini of the FPET RNA with PNK and polyadenylating the RNA with EPAP;

(b) hybridization of the polyadenylated fragmented RNA obtained in step (a) to a solid phase bead format; the step easily enables an optional step of enriching for mRNA by removing rRNA sequences through hybridization prior to step (c);

(c) conversion of the bead immobilized RNA in step (b) to cDNA and subsequently to double-stranded DNA;

(d) amplification of the RNA by subjecting the double-stranded DNA obtained in step (c) to in vitro transcription with a RNA polymerase. Performing steps (c) and (d) on beads also decreases cleanup time between enzymatic steps;

(e) reduction of the starting FPET RNA sample size from 200 ng to 50 ng;

(f) ability to archive the FPET RNA libraries as bead-immobilized double-stranded DNA and to reamplify the material to produce additional RNA.

The improvements are illustrated in FIG. 13. The process starts with FPET RNA, generally 50-200 ng, and involves 1) unblocking of the 3'OH on the terminal nucleotide with PNK, 2) direct EPAP poly A tailing of the FPET RNA 3' without cleanup from PNK step, 3) hybridization of polyadenylated FPET RNA to oligo dT-T7 RNA polymerase promoter sequences immobilized to beads followed by 4) cDNA synthesis with RT, 5) partial RNA degradation by RNAse H and second strand DNA synthesis with DNA polymerase I and 6) RNA amplification by in vitro transcription. An optional procedure for a second round of IVT is shown in step 7 (broken arrows). Another optional step, shown in step 2' involves depletion of ribosomal rRNA fragments (dotted arrow).

The beads used for nucleic acid hybridization can be commercially available microbeads, such as, for example, Dynal 2.8-μm magnetic streptavidin beads (M-280) or Dynabeads® MyOne™ Streptavidin (Dynal Biotech, Oslo, Norway). Streptavidin beads can be easily attached to 5' or 3' biotinylated nucleic acids. Bead-based immobilized oligo dT has been quite useful in purifying mRNA (Homes, E. and Korsnes, L. (1990), *Genet. Anal. Tech. Appl.* 7:145; Jacobsen, K., Breivold, E. and Homes, E. (1990) *Nucleic Acids Res.* 18:3669) and for subsequent aRNA amplification (Eberwine, J. (1995), *Biotechniques* 20:584).

Further details of the invention, including dephosphorylation of the 3' terminus of fragmented RNA, polyadenylation, subsequent reverse transcription using extended primers, and enhanced PCR are illustrated by the following non-limiting Examples.

REFERENCE EXAMPLE 1

In Example 1 below, the following methods were used.
FPET RNA Extraction Procedure
RNA was extracted from 3-10 μm sections (for each patient). Paraffin was removed by xylene extraction followed by ethanol wash. RNA was isolated from sectioned tissue blocks using the MasterPure™ Purification kit (Epicentre Technologies, Madison, Wis.) and included a DNase I step. FPET RNA was further purified by filtration through a CHROMA SPIN™ DEPC-H20 30 column as described by suppliers (Clontech, Palo Alto). Briefly, 30 μl of 50-300 ng/μl FPET RNA was loaded onto a column (pre-spun at 2500 rpm (664×g) for 5 min. in a 5417C eppendorf centrifuge), spun through the column (same conditions as the pre-spin) and stored at −80° C. FIG. 2 shows an example of RNA isolated from formalin fixed, paraffin embedded (FPE) breast cancer samples that were archived from 1 to 17 years.

Positive Control Complementary RNA (cRNA) Synthesis
Small RNA fragments complementary to amplicons for the genes HER2, GAPDH, and CYP were generated in two steps: 1) single-stranded DNA fragments complementary to the amplicons for these genes and containing a T7 RNA polymerase site on their 5' end were synthesized (IDT, Coralville, Iowa) and amplified by PCR. 2) The PCR products were purified using CHROMA SPIN™ TE-30 columns and cRNA was generated via the AmpliScribe™ T7 Transcription kit (Epicentre Technologies) and purified using CHROMA SPIN™ DEPC-H$_2$O 30 columns.

Dephosphorylation of the FPET RNA 3' Terminus
The 3'-terminus of the FPET RNA was treated with either T4 polynucleotide kinase (PNK) or 0.01M HCl and calf alkaline phosphatase (CIP) to remove 2'-3' cyclic phosphates, 2'-monophosphates and 3'-monophosphates. These various phosphate esters are typically found on the 3' terminal ribose moiety of degraded RNAs and need to be removed to ensure efficient poly A addition to the 3' terminus of the FPET RNA.

PNK Treatment

In a 20 µl reaction volume, 100-5000 ng of FPET RNA is incubated at 37° C. for 1 h with 20 units of PNK (NEBiolabs, Beverly, Mass.) in 1×PNK buffer (70 mM Tris-HCl pH 7.6, 10 mM $MgCl_2$, 5 mM dithiothreitol) and 40 units of RNase-OUT™ (Invitrogen, Carlsbad, Calif.). The reaction is terminated by addition of 20 µl of RNAse free H20 and extraction with 40 µl of phenol: $CHCl_3$:IAA (25:24:1) pH 6.6 (Ambion, Inc., Austin, Tex.). After centrifugation at 14,000×g for 1-2 min., the aqueous phase is removed, passed over a CHROMA SPIN™ DEPC-H2O 30 column and volume reduced to 12.5 µL using a Savant speed vacuum.

CIP Treatment

In a 20 µl reaction volume, 100-5000 ng of FPET RNA is incubated for 2 hrs in 10 mM HCl at 25° C. The FPET RNA is then passed over a CHROMA SPIN™ DEPC-H2O 30 column as above and incubated with 10 units of CIP (New England Biolabs, Beverly, Mass.) for 30 min at 37° C. in 1×NEBuffer 3 (10 mM NaCl, 5 mM Tris-HCl, pH 7.9, 1 mM $MgCl_2$, 1 mM dithiothreitol) and 40 units of RNaseOUT™ (Invitrogen, Carlsbad, Calif.). The reaction is terminated by addition of 20 µl of RNAse free $H_2O$ and extraction with 40 µl of phenol: $CHCl_3$:IAA (25:24:1) pH 6.6 (Ambion Inc., Austin, Tex.). After centrifugation at 14,000×g for 1-2 min., the aqueous phase is removed, passed over a CHROMA SPIN™ DEPC-H2O 30 column and volume reduced to 12.5 µL using a Savant speed vacuum.

Polyadenylation of FPET RNA 100-5000 ng of dephosphorylated FPET RNA was incubated at 37° C. (20 µL rxn volume) with 1.0 unit of *E. coli* poly A polymerase (EPAP) in 1×EPAP buffer (Ambion Inc., Austin Tex.), 1 mM ATP and 40 units of RNAseOUT™ (Invitrogen, Carlsbad, Calif.) for 15 min. The reaction was terminated by addition of 20 µl of RNAse free $H_2O$ and extraction with 40 µl of phenol: $CHCl_3$:IAA (25:24:1) pH 6.6 (Ambion Inc., Austin, Tex.). After centrifugation at 14,000×g for 1-2 min., the aqueous phase was removed and passed over a CHROMA SPIN™ DEPC-H2O 30 column.

FPET RNA Analysis

RNA was quantitated using the RiboGreen fluorescence method (Molecular Probes). RNA size was analyzed by microcapillary electrophoresis using the Agilent 2100 Bioanalyzer (Agilent Technologies, CA).

TaqMan® Primer/Probe

For each gene, we identified the appropriate mRNA reference sequence (REFSEQ) accession number for the gene and accessed the sequences through the NCBI Entrez Nucleotide database. Primers and probes were designed using Primer Express (Applied Biosystems, Foster City, Calif.) and Primer 3 programs [Steve Rozen and Helen J. Skaletsky (2000), Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386]. Oligonucleotides were supplied by Biosearch Technologies Inc. (Novato, Calif.) and Integrated DNA Technologies (Coralville, Iowa). Amplicon sizes were limited to 85 bases. Fluorogenic probes were dual-labeled with 5'-FAM and 3'-BHQ1.

Reverse Transcription

Reverse transcription was carried out using a SuperScript™ First-Strand Synthesis Kit for RT-PCR (Invitrogen Corp., Carlsbad, Calif.). The reactions were carried out with total FPET RNA (3-50 ng/µL) and either pooled gene specific primers (100 nM each) or oligo(dT) primers (25 ng/µl) or oligo(dT)-T7 primers (0.25-5.0 µM). For the extended primer reverse transcription, the reaction was performed using the Omniscript Reverse Transcriptase for First-strand cDNA synthesis kit (Qiagen, Valencia, Calif.) as described. Total FPET RNA (3-50 ng/µL) and pooled extended gene specific primers were used at concentrations of 3-50 ng/µL and 100 nM (each primer), respectively.

Second Strand DNA Synthesis $1^{st}$-strand cDNA synthesis products derived from 100-5000 ng FPET RNA were incubated at 16° C. (150 µL reaction volume) in 1× second strand buffer [20 mM Tris-HCl, pH 6.9; 4.6 mM MgCl2; 90 mM KCl; 0.15 mM β-$NAD^+$; 10 mM $(NH_4)_2SO_4$], 0.2 mM dNTP mix, 10 units DNA ligase, 40 units DNA polymerase 1, and 2 units RNase H (all reagents Invitrogen, Carlsbad, Calif.) for 2 hours. 9 units T4 DNA polymerase (NEBiolabs) were then added; reaction mix was incubated an additional 15 minutes. DNA was precipitated with 5M ammonium acetate and 100% ethanol, with 5 µg of glycogen as a carrier.

In Vitro Transcription (IVT)

The precipitated ds-DNA (from above) was resuspended in 8 µL nuclease-free $H_2O$ and an IVT reaction (20 µL total) was performed using MEGAscript™ T7 kit (Ambion, Austin Tex.) and allowed to proceed for 4 hours at 37° C. Subsequently, reaction volume was increased to 40 µL with nuclease-free H2O and cRNA was precipitated with 3M sodium acetate and 100% ethanol. Precipitated cRNA was resuspended in 20-40 µL nuclease-free H2O.

TaqMan® Gene Expression Profiling

For ABI 7900® runs, the TaqMan® reactions were performed in duplicate 5 µl reactions consisting of 1× Universal PCR Master Mix and cDNA made from an equivalent of 1 ng of total RNA. Final primer and probe concentrations were 0.9 µM (each primer) and 0.2 µM, respectively. PCR cycling was carried out on the ABI Prism® 7900 as follows: 95° C. 10 minutes×1 cycle, 95° C. 20 seconds, 60° C. 45 seconds×40 cycles. For 7700 runs, the TaqMan® reactions were performed in triplicate 25 µl reactions consisting of 1×PCR buffer A, 4 µM $MgCl_2$, 0.2 µM dNTPs, 0.025 U/µl AmpliTaq Gold™ DNA polymerase (Applied Biosystems, Foster City, Calif.), and cDNA made from an equivalent of 2.5 ng of total RNA. Final primer and probe concentrations are as above. PCR cycling was carried out on an ABI Prism® 7700 as above. For the modified PCR priming experiments, PCR cycling was carried out on the ABI Prism® 7700 as follows: 95° C. 10 minutes×1 cycle, 95° C. 20 seconds, 50° C. 2 minutes×2 cycles, 95° C. 20 seconds, 60° C. 45 seconds×38 cycles.

EXAMPLE 1

Standard Protocol

Figure 6:
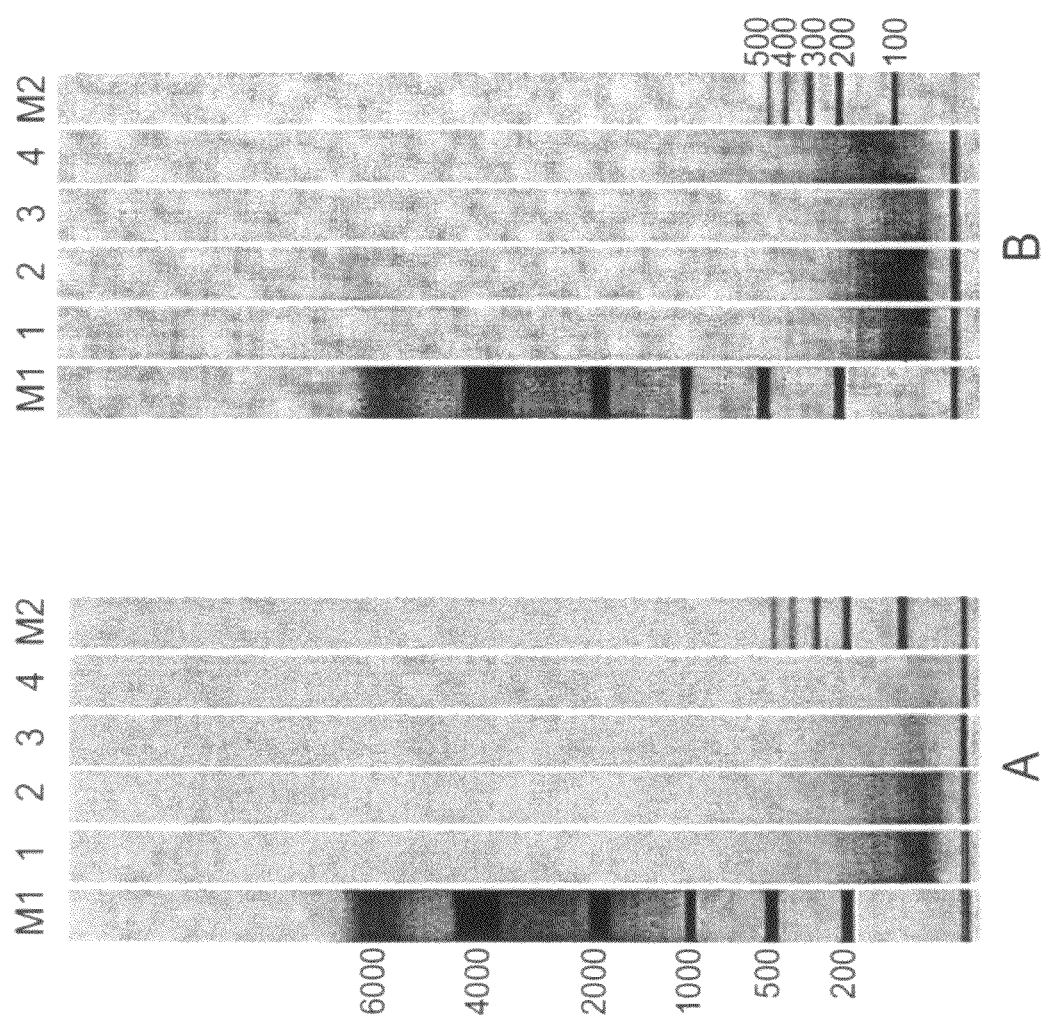
FIG. 6A shows a gel image of FPET RNAs that have been treated with PNK (lane 1), PNK buffer control (lane 2), CIP (lane 3) or CIP buffer control (lane 4).
FIG. 6B shows a gel image of FPET RNAs that have been treated with PNK buffer control followed by EPAP buffer control (lane 1), PNK followed by EPAP buffer control (lane 2), PNK buffer control followed by EPAP, or PNK followed by EPAP (lane 4). Samples were analyzed by capillary electrophoresis on an Agilent 2100 using an RNA 6000 Nanochip. Lanes M1 and M2 show RNA markers with the size of each band denoted in bases.

RNA was treated with polynucleotide kinase (PNK) or calf intestinal alkaline phosphatase (CIP), enzymes with 2'-3' cyclic phosphatase activity and 3' phosphatase activity, respectively. Capillary electrophoretic [Agilent 2100] analysis of the treated FPET RNA suggested that treatment of the FPET RNA with PNK or CIP removed the blocking phosphates, as judged by a subtle decrease in the mobility of the enzyme-treated RNA relative to that of the untreated RNA (FIG. 6A). Decreased electrophoretic mobility was expected because removal of the charged phosphate group would have decreased the charge/mass ratio of the FPET RNA.

If the blocking phosphates from the 3' end of the FPET RNAs were effectively removed, then polyadenylation of the RNA should be possible. Treatment of FPET RNA with PNK followed by EPAP treatment (+PNK/+EPAP) resulted in a significant decrease in electrophoretic mobility of the FPET RNA (FIG. 6B). To confirm that the mobility shift was due to polyadenylation and not simply due to dephosphorylation, PNK treatment alone (+PNK/−EPAP) and a no treatment (−PNK/−EPAP) controls were included. The only significant decrease in mobility was noticed with both PNK and EPAP treatment. Thus, the combination of an unblocking, dephosphorylation step (PNK or CIP treatment) followed by a polyadenylation step by EPAP most likely converted the FPET RNA to a polyadenylated form efficiently. This polyadenylated RNA should be suitable for universal cDNA synthesis using oligo dT primers and RT.

Figure 7:
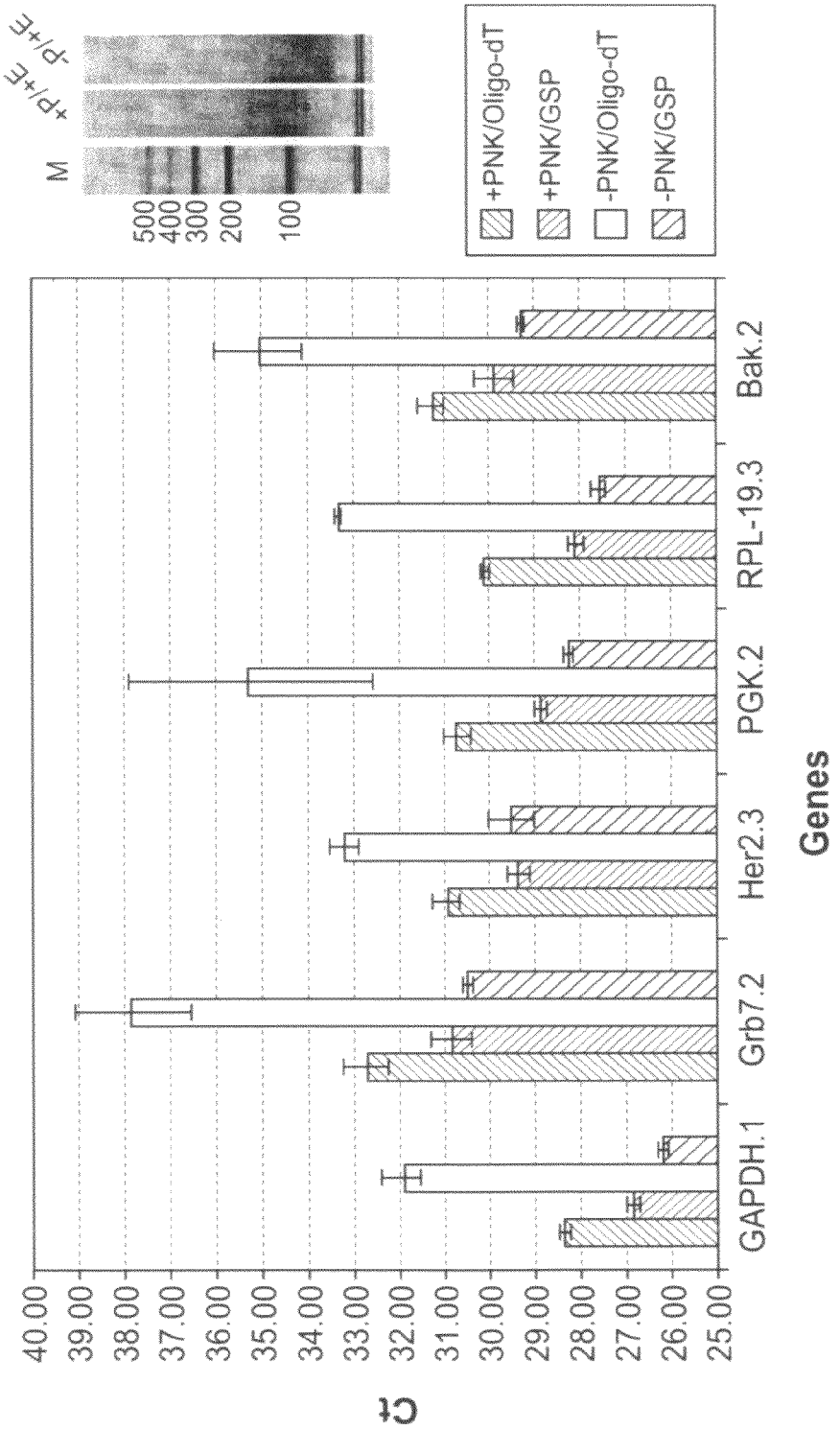
FIG. 7 shows a selected gene expression analysis of breast tumor FPET RNA. Expression was analyzed by real time quantitative RT-PCR (TaqMan®) on an ABI Prism® 7700.

To test the effectiveness of polyadenylation on universal cDNA synthesis, FPET RNA was polyadenylated by EPAP following treatment with or without PNK or CIP, and the cDNA abundance was measured by TaqMan® RT-PCR. PNK (FIG. 7) or CIP (FIG. 8) treatment followed by polyadenylation and oligo-dT primed RT-PCR resulted in a significant increase in cDNA yields relative to non-PNK (4-32 fold) or non-CIP (8-16 fold) treated samples. This indicated that unblocking the 3' end dramatically increases the efficiency of polyadenylation and oligo dT primed cDNA synthesis. As expected, polyadenylation had very little effect on GSP primed cDNA synthesis. Importantly, the GSP positive controls indicated that this universal priming method amplified cDNA 25-50% as effectively as the currently most effective priming method, GSP priming.

In a further experiment, cDNA was synthesized from polyadenylated FPET RNA (PNK and EPAP treated) and non-polyadenylated FPET RNA using either oligo dT primers or GSP primers, respectively. In this experiment, 96 pooled GSP primers were used and expression of 96 genes was analyzed by TaqMan® RT-PCR (using 1 ng FPET RNA/well, 384 wells; ABI Prism® 7900 instrument). The data shown in FIG. 9 demonstrate that polyadenylated FPET RNA was efficiently converted to cDNA (pA-dT) as judged by the similarity in Ct values to GSP-primed (pA_GSP1) cDNA. For many genes, the polyadenylated FPET RNA gave a better signal with oligo dT priming than GSP priming. Table 1 shows a statistical summary of the data from FIG. 9. The left panel indicates that polyadenylating the FPET RNA prior to RT with oligo dT results in detection of 77% of the genes (Ct<38) whereas nonpolyadenylated RNA yields only 16% detectable genes. Furthermore, there is a significant correlation between the gene expression profile of cDNA generated by GSP and oligo dT priming of polyadenylated RNA (Pearson R=0.77). There was no correlation between gene expression profiles of cDNA generated by GSP and nonpolyadenylated, oligo dT primed RT (R=0.11).

Another useful improvement to this method was the inclusion of a T7 RNA polymerase site on the oligo dT primer such that FPET RNA could be universally amplified following polyadenylation. FIG. 10 (A-C) demonstrates the effect of polyadenylation and in vitro transcription (IVT) [T7 RNA polymerase amplification (Van Gelder et al., Proc. Natl. Acad. Sci. USA 87(5):1663-7 (1990)] on the expression of a 46 genes from three different RNA sources. FIG. 10A shows expression profiles from high quality intact RNA (Stratagene). IVT increased the average TaqMan signal of all 46 genes (see inset) ~6 fold when comparing cDNA generated by GSP primed RT (GSP; non-amplified control) and cDNA generated by oligo dT-T7 primed RT that was subsequently amplified by IVT (No EPAP IVT). Polyadenylation of the RNA prior to cDNA synthesis and IVT had no additional effect on the overall TaqMan signal (EPAP IVT-1 and IVT-2). FIGS. 10B and 10C show gene expression profiles generated from moderately degraded FPET RNA (BioPath Placenta) and badly degraded FPET RNA (Clinomics 168), respectively. In these cases, polyadenylation was a necessary step for IVT amplification of the RNA. As shown, the average TaqMan signals from duplicate experiments (EPAP IVT avg) were ~2.5 Cts lower (6 fold) than signals generated by IVT from non-polyadenylated RNA (No EPAP IVT). Importantly, the gene profiles are maintained after IVT as indicated by the Pearson correlation coefficient (R=0.91-0.96). In summary, polyadenylation of degraded FPET RNA is a useful method to globally synthesize cDNA corresponding to each gene present in the sample. This cDNA can be used to further amplify gene signals accurately and reproducibly by IVT.

Another improvement for enhancement of gene expression signals is shown in FIG. 12. In this example, the detection of six genes was enhanced as the primers were lengthened. Extending the primer lengths to 20-30 bases beyond the standard reverse primer (GSP) length, increased the gene expression signals from 10-15 fold. In addition, if the first two cycles of the subsequent PCR were performed at 50° C. rather than 60° C., the gene expression signals further increased several fold.

REFERENCE EXAMPLE 2

Unless otherwise indicated, in Examples 2-5 below, the following materials and methods were used.

Materials

MyOne Streptavidin-Coated Microspheres: Dynal, 2 mL @ 10 mg/mL.

Biotin-Eberwine Primer: IDT, 100 pmol/uL stock (100 uM). 5'-Biotin-

```
                                            (SEQ ID NO: 1)
GGCCAGTGAATTGTAATACGACTCACTATAGGGAGGCGGTTTTTTTTTT

TTTTTTTTTTTVN-3'
```

T4 Polynucleotide Kinase (PNK): New England BioLabs, 2,500 units @ 10 U/μL. Comes w/a 10× reaction buffer.

RNase Inhibitor: Applied Biosystems, 20 U/mL.

Nuclease-free $H_2O$: Ambion.

Poly(A) Tailing Kit: Ambion. Items used in kit-E. Coli poly(A) polymerase (EPAP) enzyme (2 U/μL), 5× reaction buffer, 10 mM ATP.

Superscript RT First-Strand System: Invitrogen. Items used in kit-10×RT buffer, 0.1M DTT, 10 mM dNTP mix (note: dNTP mix is also used in second-strand synthesis), 2 U/μL RNase H (used in second strand synthesis).

Superscript II RT enzyme: Invitrogen, 200 U/μL. Comes with 5×RT buffer, which is used to create 1×RT buffer for pre-RT washing step.

0.1M $MgCl_2$: Ambion. Comes as 1M stock and is subsequently diluted 1:10

5× Second Strand Buffer: Invitrogen. DNA Ligase: Invitrogen, 10 U/μL.

DNA Polymerase I: Invitrogen, 10 U/μL.

T4 DNA Polymerase: Invitrogen, 5 U/μL.

Glycogen: Ambion, 5 mg/mL.

5M ammonium acetate: Ambion.

100% ethanol: SigmaMEGAScript-T7 IVT Kit: Ambion. Items used in kit-10×IVT buffer, 75 mM NTPs, enzyme mix.

3M sodium acetate: Ambion.

Methods

PNK and EPAP Treatment

For 200-300 ng of FPET RNA: FPET RNA was incubated in 1×PNK buffer (70 mM Tris-HCl pH 7.6, 10 mM $MgCl_2$, 5 mM dithiothreitol), 1 U/µl RNase Inhibitor (Applied Biosystems, Foster City, Calif.) and 1 U/µl of PNK (NEBiolabs, Beverly, Mass.) at 37° C. for 30 min in a 20 µl reaction volume. Following PNK treatment, the FPET RNA was directly polyadenylated by adding to the reaction mixture to a final concentration; 1×EPAP buffer (Ambion, Austin, Tex.), 1 mM ATP, 1.5 U/µl RNase Inhibitor and 0.025 U/µl EPAP (Ambion, Austin, Tex.). The mixture was incubated at 37° C. for 15 min in a 40 µl reaction volume, then at 70° C. for 5 min.

For 50 ng of FPET RNA: PNK and EPAP treatment were identical to above, except for reaction volumes, which were scaled down to 5 µl and 10 µl (¼ volume), respectively.

Reverse Transcription of Polyadenylated FPET RNA with T7-Oligo dT Primer-Magnetic Bead Complex Preparation of T7-Oligo dT Primer-Magnetic Bead Complexes Dynabeads® MyOne™ Streptavidin (Dynal Biotech, Oslo, Norway) stock bead container was removed from 4° C. storage and vortexed vigorously to fully resuspend the beads. 40 µL (400 µg) beads were removed to a 0.5 mL microcentrifuge tube; spin beads down in a tabletop microcentrifuge (<5 sec) to collect liquid in bottom of tube. Avoid overcentrifuging tubes containing paramagnetic beads, as it will cause them to pellet and aggregate, which can reduce bead performance. Tubes were placed in a MPC-S magnetic rack (Dynal Biotech, Oslo, Norway) with the tube hinges facing the magnet and allow beads to collect against side of tube (~2 min). Tubes were opened without removing from rack; and the supernatant was pipetted off. Tubes were removed from rack; beads were washed by resuspending in 100 µL 1× B&W buffer (5 mM Tris-HCl pH 7.3, 0.5 mM EDTA, 1M NaCl). Tubes were spinned down briefly to collect liquid, then placed in magnetic tube rack. Beads were allowed to collect against side of tube and supernatant was removed as above; and 1× B&W buffer wash repeated for a total of two washes. Final wash supernatant was removed, then beads were resuspended in 40 uL 1× B&W buffer containing 25 uM Eberwine T7 oligo dT primer (5'-Biotin GGCCAGTGAATTGTAATACGACT-CACTATAGGGAGGCGGTTTTTTTTTTTTTTTTTTTT-TTVN-3'). (SEQ ID NO: 1) Incubation was performed at room temperature for 15 min on an Eppendorf thermomixer (850 rpm). Beads were suspended on magnet (~2 min); supernatant was removed and beads were washed two times w/100 µL 1× B&W buffer. Beads were resuspended in 80 µL Bead Storage Buffer (1×PBS, 70% EtOH) and stored at 4° C. until ready for use.

Hybridization of T7-Oligo dT Beads to Polyadenylated FPET RNA

For 200-300 ng of FPET RNA: During PNK/EPAP incubations, the previously prepared primer-bead solution was removed from 4° C. storage. The tube was flicked to resuspend beads and spinned down briefly to collect liquid. 20 µL (100 µg) of beads were aliquoted into a 0.5 mL tube and the tube placed on magnet for about 2 minutes. The supernatant was removed; beads were washed twice with 100 µL 1× B&W Buffer. The final wash supernatant was removed during the 70° C. EPAP inactivation step. After the 70° C. incubation was completed, the tube containing the EPAP reaction was thoroughly spinned down to collect liquid, then the reaction contents transferred to tube containing primer-bead complex. The tube was flipped to resuspend beads and briefly spinned down; incubated at room temperature on thermomixer (850 rpm) for 5 minutes. The tube was placed on magnetic rack for about 2 minutes; the supernatant was removed.

For 50 ng of FPET RNA: Same as above except aliquot 5 µL (25 ug) of beads.

First-Strand cDNA Synthesis

Reverse transcription was carried out using a SuperScript™ First-Strand Synthesis Kit for RT-PCR (Invitrogen Corp., Carlsbad, Calif.).

For 200-300 ng of FPET RNA: Beads were washed once with 100 µL 1×RT buffer (20 mM Tris-HCl pH 8.4, 50 mM KCl). Beads were resuspened in 20 µL RT reaction mix consisting of 1×RT buffer, 5 mM $MgCl_2$, 10 mM DTT, 0.5 mM dNTPs, 1 U/µL RNase inhibitor, and 10 U/µL SuperScript II RT and incubate at 42° C. on thermomixer (850 rpm) for 50 min.

For 50 ng of FPET RNA: Same as above except beads were resuspended in 5 µL 1×RT buffer.

Second-Strand cDNA Synthesis

For 200-300 ng of FPET RNA: First strand cDNA reaction was removed from thermomixer and 130 µL of the following second strand reaction mix added: 1.15× second strand buffer, 0.23 mM dNTP mix, 0.077 U/µL DNA ligase, 0.31 U/µL DNA polymerase I and 0.015 U/µL RNase H. Flick tube to mix; spin down briefly. Incubate for 2 hrs at 16° C. on thermomixer (850 rpm).

For 50 ng of FPET RNA: Same as above except 32.5 µL of the second strand reaction mix is added.

Second-Strand DNA Cleanup/In Vitro Transcription

For both 200/300 ng and 50 ng of FPET RNA: Second-strand reaction tube was removed from thermomixer; spinned down briefly and place on magnetic rack for about 2 minutes. Supernatant was removed and beads washed twice with 100 µL 1×IVT wash buffer (400 mM Tris pH 7.3, 70 mM $MgCl_2$, 100 mM NaCl, 20 mM spermidine).

The MEGAScript-T7 IVT kit (Ambion, Austin Tex.) was used for in vitro transcription. Resuspend beads in 20 uL IVT master mix (prepared as described by Ambion) and flick tube to mix. Spin down briefly and incubate at 37° C. for 4 hrs on thermomixer (1000 rpm).

IVT Cleanup

The tube was removed from thermomixer; spinned down briefly and placed on magnetic rack for about 2 minutes. The supernatant was transferred to a 1.5 mL microcentrifuge tube and the following reagents added in order:

| | |
|---|---|
| Nuclease-free $H_2O$: | 20 µL |
| 5 mg/mL glycogen (Ambion): | 1 µL |
| 3M sodium acetate (Ambion): | 4 µL |
| 100% ethanol (Sigma): | 100 µL |

The tube was vortexed and incubated @ −20° C. from 1 hr to overnight. The tube was spinned down in a refrigerated Eppendorf centrifuge @ 14,000 rpm for 20 min (4° C.) to pellet cRNA. The supernatant was removed and 500 µL 70% ethanol solution was added to wash pellet. The tube was spinned down in a refrigerated Eppendorf centrifuge @ 14,000 rpm for 3 min (4° C.). With a pipet, as much alcohol was removed from the tube as possible, then the tube left (with top open) in a fume hood to allow remaining alcohol to evaporate (5-10 min). cRNA pellet was resuspended in 40 µL nuclease-free $H_2O$.

FPET RNA Analysis

RNA was quantitated using the RiboGreen fluorescence method (Molecular Probes). RNA size was analyzed by microcapillary electrophoresis using the Agilent 2100 Bioanalyzer (Agilent Technologies, Calif.).

TaqMan® Gene Expression Profiling

TaqMan® reactions were performed in duplicate 5 µl reactions consisting of 1× Universal PCR Master Mix and 1 ng of cRNA. Final primer and probe concentrations were 0.9 µM (each primer) and 0.2 µM, respectively. PCR cycling was carried out on the ABI Prism® 7900 as follows: 95° C. 10 minutes×1 cycle, 95° C. 20 seconds, 60° C. 45 seconds×40 cycles.

EXAMPLE 2

Removal of the Cleanup Step Between Dephosphorylation and Polyadenylation of the FPET RNA 3' Terminus The 3'-terminus of the FPET RNA is treated with T4 polynucleotide kinase (PNK) to remove 2'-3' cyclic phosphates, 2'-monophosphates and 3'-monophosphates. These various phosphate esters are typically found on the 3' terminal ribose moiety of degraded RNAs and need to be removed to ensure efficient poly A addition to the 3' terminus of the FPET RNA.

As previously described, the standard dephosphorylation step with PNK is terminated by addition of 20 µl of RNAse free $H_2O$ and extraction with 40 µl of phenol:$CHCl_3$:IAA (25:24:1) pH 6.6 (Ambion, Inc., Austin, Tex.). After centrifugation at 14,000×g for 1-2 min., the aqueous phase is removed, passed over a CHROMA SPIN™ DEPC-$H_2O$ 30 column and volume reduced to 12.5 µL using a Savant speed vacuum. The RNA is now ready for the standard polyadenylation reaction with EPAP in a 20 µl volume.

To streamline the method, we several modifications to the procedure were tried, as shown in FIG. 2. Following the PNK reaction using 1000 ng of breast cancer FPET RNA (Clinomics), six cleanup conditions were tested prior to polyadenylation with EPAP. Cleanup condition 1 is essentially the same as the standard protocol discussed earlier, but with the sample volume reduction step omitted (speed-vac). This results in a larger sample volume and thus required an increase in the final EPAP reaction volume (40 µl). The 40 µl reaction volume was kept constant for all five cleanup conditions as shown in FIG. 14. Microcapillary electrophoresis analysis (FIG. 14, left panel) of the polyadenylated RNAs following the five modified cleanup conditions indicated that on average, 50-140 adenylates were added to the RNAs relative to the starting material (SM), which had an average size of 90 nucleotides (nt); For example, for condition 1; 150–90=60 adenylates. These results indicate that all five conditions yielded polyadenylated FPET RNA of acceptable size. Interestingly, the percent of RNA recovered after the EPAP cleanup step indicated that all five PNK cleanup conditions were better than the standard method, condition 6 (FIG. 14, lower right). Furthermore, the no cleanup condition (5) gave the highest yield. The percent recovery is relative to input RNA and in some cases is greater than 100% due to an increase in mass from polyadenylation. To further assess the quality of the polyadenylated RNAs, four samples were carried through the remainder of the standard IVT process and expression profiled by TaqMan® RT-PCR as outlined in our previous patent application (39740.0003PR). FIG. 15 shows a 47 gene panel profile of the amplified RNAs for conditions 2-5. All profiles showed a high concordance (R≧0.91) with unamplified RNA (SM) and standard treated RNA (condition 6). The no cleanup condition 5 gave the lowest average Ct (36.0) and the highest IVT yield (95.8 µg) and thus was adopted as the standard procedure for EPAP treatment (step 2, FIG. 13).

EXAMPLE 3

Hybridization of Polyadenylated FPET RNA to T7 Promoter-Oligo dT Beads, Double-Strand cDNA Synthesis and IVT Another improvement to the standard method of the present invention includes the hybridization of the polyadenylated FPET RNA to T7 promoter-oligo dT primers that are conjugated to magnetic polystyrene beads. This enables all subsequent enzymatic steps to be easily performed on a solid support with minimal cleanup steps. For instance, it eliminates the need for phenol-$CHCl_3$ extractions and spin column chromatography between reactions. The use of beads also lends itself to automated process that could greatly increase the throughput. In addition, archived, bead conjugated-cDNA libraries can be easily re-amplified to yield additional cRNA. FIG. 16 shows the 47 gene expression profile for placental cRNAs generated by the standard solution, non-bead based IVT method (free IVT) and cRNA generated by the solid phase, bead based IVT method (solid-phase IVT) outlined in FIG. 13. For comparison, non-amplified placental FPET RNA is also shown (SM). Again, both IVT processes yielded cRNA that displayed a high concordance with untreated RNA (R≧0.94). Although the traditional non-bead IVT method yielded 1.74 times more cRNA than the bead based IVT method, the average Ct was 0.74 higher. When the amounts of RNA are adjusted to yield the same average Ct as starting material RNA, the relative yields (Ct adjusted) are approximately equal (21.66 vs. 20.79). Thus, the bead based IVT method is nearly as efficient as the non-bead based method in terms of amplification and fidelity. Although both IVT methods do not achieve the same level of RT-PCR sensitivity (avg. Ct/mass RNA) as starting material when using equivalent amounts of RNA (1 ng/well), they still are achieving a 100-fold amplification of RNA after adjusting for the loss of sensitivity.

EXAMPLE 4

A Comparison of RNA Amplification Using 50 ng and 200 ng FPET RNA

Archived FPET samples with clinical histories are extremely valuable for retrospective clinical studies. As such, it is often difficult to obtain more than 1 or 2 five-micron FPET sections per patient from clinical collaborators for studies. Thus, there is a need to optimize IVT amplification of FPET RNA starting from less than a microgram of RNA and preferably less than 100 ng RNA. FIG. 17 shows the 47 gene expression profile from 200 ng (condition 1) and 50 ng (conditions 2 and 3) of FPET RNA amplified by the bead-based protocol. For the first 50 ng RNA amplification (condition 2), the ratio of RNA to bead mass and the reaction volumes of each step were identical to the standard 200 ng RNA amplification. For the second 50 ng RNA amplification (condition 3), the ratio of RNA to bead mass was identical, but the reaction volumes were scaled down proportionally to ¼ of the volume. Both 50 ng RNA amplications yielded approximately the same amount of cRNA, although 10-fold less than the 200 ng RNA amplification. If we expect a 4-fold lower yield from the 50 ng reactions, since we started with ¼ the amount of FPET RNA, then we still have an unaccounted 2.5-fold loss in efficiency when scaling down our amplication from 200 ng to 50 ng of FPET RNA. However, both expression profiles derived from the 50 ng amplication still show a strong correlation with the 200 ng RNA amplification (R≧0.97). Also, the average Ct for the 50 ng volume-scaled amplification (condition 3) was equivalent to the 200 ng RNA amplification. Thus, the scaled down (¼ vol) version was adopted as the 50 ng FPET RNA amplification procedure.

EXAMPLE 5

A comparison of a Secondary Amplification Using 50 ng and 200 Nanogram of FPET RNA As previously mentioned, an additional benefit of archiving cDNA FPET libraries on beads is that they can be easily reamplified. As an example of a secondary IVT, archived beads containing conjugated cDNA from the above experiment, were washed once, resuspended in IVT buffer and amplified according to the original IVT protocol. FIG. 17b shows the results of this experiment. Again, both 50 ng RNA amplications yielded approximately the same amount of cRNA, although 10-fold less than the 200 ng RNA amplification. In addition, all three secondary amplifications yielded about ⅓ as much RNA as their corresponding primary amplifications. A high level of fidelity was maintained between the three secondary amplifications (R≧0.95). The primary and secondary amplifications for each individual condition also maintained a high level of concordance (R≧0.97). The expression profiles for the condition 3 (FRA-¼ vol: 50 ng/25 ug) primary and secondary IVTs are shown in FIG. 17c.

All references cited throughout the present disclosure are hereby expressly incorporated by reference.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

What is claimed is:

1. A method for preparing fragmented RNA comprising a multiplicity of RNA species for gene expression analysis comprising the steps of:
   (a) producing randomly primed first strand cDNA from total RNA obtained from a fixed paraffin-embedded tissue (FPET) sample obtained from a human subject, using reverse transcriptase and random primers;
   (b) tailing said randomly primed first strand cDNA to produce tailed first strand cDNA, wherein said tailing is done using poly(A) polymerase or terminal transferase;
   (c) converting said tailed first strand cDNA to double stranded cDNA using a primer that anneals to said tail and contains a promoter sequence for an RNA polymerase;
   (d) transcribing said double stranded cDNA using said RNA polymerase to produce amplified RNA;
   (e) reverse transcribing said amplified RNA using a reverse transcriptase and random primers to produce a nucleic acid sample comprising amplified cDNA and amplified RNA; and
   (f) degrading said amplified RNA in said nucleic acid sample, thereby producing a DNA sample comprising amplified cDNA.

2. The method of claim 1 wherein the size of the total RNA comprises RNA fragments of between about 20 bases and about 2000 bases in length.

3. The method of claim 1 where the average size of the total RNA comprises RNA fragments of between about 50 and about 300 bases in length.

4. The method of claim 1 wherein said tailing is polyadenylating.

5. The method of claim 1, wherein said reverse transcriptase is selected from the group consisting of avian myeloblastosis virus reverse transcriptase (AMV-RT), Moloney murine leukemia virus reverse transcriptase (MMLV-RT), and recombinant heterodimeric reverse transcriptases expressed in *E. coli*.

6. The method of claim 1 wherein said RNA polymerase promoter is a T7 RNA polymerase promoter.

7. The method of claim 1 wherein said FPET sample of tissue comprises a sample of a tumor.

---

SEQUENCE LISTING

```
<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: oligonucleotide dT primer
<220> FEATURE:
<221> NAME/KEY: misc_feature
<222> LOCATION: 63
<223> OTHER INFORMATION: n= a, t, g or c

<400> SEQUENCE: 1
ggccagtgaa ttgtaatacg actcactata gggaggcggt tttttttttt tttttttttt    60 tvn                                                                  63
```

8. The method of claim 7 wherein said tumor is selected from the group consisting of breast cancer, color cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

9. The method of claim 1, wherein said degrading comprises treating said nucleic acid sample with RNaseH.

10. The method of claim 1, further comprising:

using said DNA sample in an RT-PCR assay to evaluate the expression of a plurality of genes.

\* \* \* \* \*